US 8,556,828 B2

(12) United States Patent
Amano et al.

(10) Patent No.: US 8,556,828 B2
(45) Date of Patent: Oct. 15, 2013

(54) BLOOD TEST DEVICE

(75) Inventors: Yoshinori Amano, Ehime (JP); Masaki Fujiwara, Ehime (JP); Takeshi Nishida, Ehime (JP)

(73) Assignee: Panasonic Corporation, Osaka (JP)

( * ) Notice: Subject to any disclaimer, the term of this patent is extended or adjusted under 35 U.S.C. 154(b) by 1468 days.

(21) Appl. No.: 12/278,825

(22) PCT Filed: Feb. 9, 2007

(86) PCT No.: PCT/JP2007/052330
§ 371 (c)(1),
(2), (4) Date: Aug. 8, 2008

(87) PCT Pub. No.: WO2007/091671
PCT Pub. Date: Aug. 16, 2007

(65) Prior Publication Data
US 2010/0168615 A1 Jul. 1, 2010

(30) Foreign Application Priority Data

Feb. 9, 2006 (JP) .................................. 2006-032245
Feb. 9, 2006 (JP) .................................. 2006-032246

(51) Int. Cl.
*A61B 5/00* (2006.01)
*A61B 17/14* (2006.01)
*A61B 17/32* (2006.01)

(52) U.S. Cl.
USPC .......................................... 600/583; 606/181

(58) Field of Classification Search
USPC ........................... 600/583, 584; 606/181, 182
See application file for complete search history.

(56) References Cited

U.S. PATENT DOCUMENTS 6,349,229 B1  2/2002  Watanabe et al.
6,537,242 B1 *  3/2003  Palmer ............................. 604/22
(Continued)

FOREIGN PATENT DOCUMENTS

| JP | 3382853 B2 | 12/2002 |
| JP | 2003-524496 A | 8/2003 |
| WO | 01/64105 A1 | 9/2001 |
| WO | 03/007819 A1 | 1/2003 |
| WO | 2004/054445 A1 | 7/2004 |

OTHER PUBLICATIONS

U.S. Appl. No. 12/159,904 to Fujiwara et al., which was filed Jul. 2, 2008.

(Continued)

*Primary Examiner* — Max Hindenburg
*Assistant Examiner* — Jonathan M Foreman
(74) *Attorney, Agent, or Firm* — Greenblum & Bernstein, P.L.C.

(57) ABSTRACT

A blood test device by which the amount of plumped skin at a puncture site for conducting a blood test or collecting blood can be controlled so that a blood component can be accurately measured. The blood test device includes: a housing; an inner tube provided in one side of the housing; a reciprocating unit which reciprocates within the inner tube; a blood collection needle connected to the reciprocating unit; a blood sensor facing to the blood collection needle and being located at the tip of the inner tube; a measurement circuit to which a signal is fed from the blood sensor; and a negative pressure unit driven by the measurement circuit. An outer tube, that is a tube covering the inner tube, has an opening in the tip side of the inner tube, is capable of moving relative to the inner tube, and is provided so as to return to a definite relative position. The negative pressure provider can apply a negative pressure to the inside of the outer tube.

30 Claims, 21 Drawing Sheets

(56) References Cited

U.S. PATENT DOCUMENTS

| | | | |
|---|---|---|---|
| 6,706,159 B2 | 3/2004 | Moerman et al. | |
| 7,378,007 B2 | 5/2008 | Moerman et al. | |
| 2002/0130042 A1* | 9/2002 | Moerman et al. | 204/403.01 |
| 2004/0215224 A1* | 10/2004 | Sakata et al. | 606/181 |
| 2005/0011759 A1 | 1/2005 | Moerman et al. | |
| 2006/0129065 A1 | 6/2006 | Matsumoto et al. | |

OTHER PUBLICATIONS

U.S. Appl. No. 12/162,612 to Fujiwara et al., which was filed Jul. 30, 2008.

U.S. Appl. No. 12/162,627 to Amano et al., which was filed Jul. 30, 2008.

English language Abstract of JP 11-347018 A.

* cited by examiner

BLOOD TEST DEVICE

TECHNICAL FIELD

The present invention relates to a blood test apparatus.

BACKGROUND ART

Diabetes patients need to measure the blood sugar level regularly and administer insulin based on the blood sugar level to maintain a normal blood sugar level. To maintain a normal blood sugar level, it is necessary to measure the blood sugar level regularly. Therefore, diabetes patients have to sample a small amount of blood from their fingertips and measure the blood sugar level from this sampled blood using a blood test apparatus.

The blood test apparatus has a blood sensor for detecting component in blood and punctures a part to be punctured that abuts on the blood sensor. Blood flowing out from the punctured part is led to the blood sensor, and the component (such as the blood sugar level) is measured.

A blood test apparatus with projecting parts that are arranged around the blood sensor to plump the part to be punctured and to make the part to be punctured abut on the sensor adequately, is known (see Patent Document 1). FIG. 25 is a cross-sectional view showing a part near the sensor of the conventional blood test apparatus. Lancet 220 attached with needle 210 is provided in housing 200 of the blood test apparatus shown in FIG. 25, and sensor 230 is provided at the end of housing 200. Skin contact ring 240 is provided around sensor 230, and skin 250, which is the part to be punctured, is plumped and is in contact with sensor 230. On the other hand, to provide body fluid from the punctured part to the sensor reliably, a body fluid test apparatus provided with a means for creating a negative pressure around the part to be punctured, is also known (see Patent Document 2).

Patent Document 1: Japanese Patent Application Publication No. 2003-524496
Patent Document 2: Japanese Patent No. 3382853

DISCLOSURE OF INVENTION

Problems to be Solved by the Invention

As described above, with the conventional blood test apparatus, to bring the skin of the part to be punctured into contact with sensor 230, part 250 to be punctured is pressed with skin contact ring 240 and part 250 to be punctured is plumped by the pressing force. However, the pressing force against the part to be punctured is difficult to be fixed, and so the amount of plumped part 250 to be punctured varies.

Therefore, the amount of the plumped skin may be fixed by providing a means for creating a negative pressure to an area around the blood sensor and maintaining the pressing force fixed by controlling the negative pressure. For example, FIG. 26 shows a blood test apparatus provided with a negative pressure means. Blood test apparatus 1 shown in FIG. 26 includes: housing 2 that forms a chassis; cylinder body 2a that is formed on one side of housing 2; plunger 3 that moves back and forth inside cylinder body 2a; handle 2b to which one end of plunger 3 is connected; latch part 2c at which handle 2b is latched; spring 2e that urges handle 2b toward tip 2d of cylinder body 2a; lancet 5 which has one end held by plunger 3 and the other end attached with blood collection needle 4; cylinder-shaped holder 6 inside which lancet 5 slides and which is inserted and fixed in cylinder body 2a; positioning convex part 6a provided in holder 6; positioning concave part 2f which is jointed with positioning convex part 6a and formed in cylinder body 2a; blood sensor 8 which is attached to one end of holder 6; measuring circuit 9 to which signals of sensor 8 are supplied; negative pressure means 11 which is connected to measuring circuit 9; and negative pressure path 11a through which the output of negative pressure means 11 is supplied to blood sensor 8.

However, even if the level of the negative pressure is fixed, the amount of the plumped part to be punctured is difficult to be fixed due to variation in the hardness of the skin of the part to be punctured. That is, as shown in FIG. 27 and FIG. 28, if the skin is hard, skin 7 is plumped slightly as shown by solid line 7a, and, if the skin is soft, skin 7 is plumped significantly as shown by dotted line 7b.

When skin 7 is plumped significantly (FIG. 28; dotted line 7b), the volume of storing part 8a of blood sensor 8 decreases. Therefore, the effective volume of storing part 8a varies depending on the amount of plumped skin 7. Therefore, cases occur where an adequate amount of blood cannot be obtained. Further, the puncturing depth of needle 4 varies depending on the amount of the plumped skin. For these reasons, cases occur where blood components may not be measured correctly.

It is therefore an object of the present invention to provide a blood test apparatus that enables maintaining the amount of the plumped skin of the part to be punctured fixed upon puncturing and blood sampling for a blood test, optimize the position of the skin to be punctured and the puncturing depth, realize reliable blood sampling and measure blood components correctly.

Means for Solving the Problem

The present invention provides a blood test apparatus having: a housing; an internal cylinder body which is formed on one side of the housing; a reciprocating section that moves back and forth inside the internal cylinder body; a blood collection needle which is connected to the reciprocating section; a blood sensor to which the blood collection needle is directed and is provided at a tip part of the internal cylinder body; a measuring circuit to which a signal of the blood sensor is supplied; and a negative pressure section which can be driven by the measuring circuit. The blood test apparatus further has an external cylinder body which covers the internal cylinder body and comprises an opening part on a tip side of the internal cylinder body, and which is arranged such that the external cylinder body is able to move relative to the internal cylinder body and return to a predetermined relative position, and in the blood test apparatus, the negative pressure section can create a negative pressure inside the external cylinder body.

Upon conducting a blood test using the blood test apparatus of the present invention, the part to be punctured is brought into contact with the external cylinder body and the external cylinder body is able to move relative to the internal cylinder body, so that, by maintaining the amount of the relative move of the external cylinder body fixed, it is possible to maintain the pressing force against the part to be punctured fixed. Further, the part to be punctured is plumped by creating a negative pressure inside the external cylinder body, and the external cylinder body is thereby moved relative to the internal cylinder body, so that, by maintaining the amount of the relative move of the external cylinder body fixed, it is possible to maintain the amount of the plumped part to be punctured fixed.

Advantageous Effect of the Invention

According to the blood test apparatus of the present invention, the amount of the plumped skin of the part to be punctured upon test (puncturing and blood sampling) can be fixed, and so the puncturing depth of the blood collection needle can be fixed and the amount of sampled blood can be fixed, so that it is possible to measure blood components correctly.

BRIEF DESCRIPTION OF DRAWINGS

FIG. 15 is an exploded plan view of the blood sensor.

FIG. 22 is a cross-sectional view showing the vicinity of the attaching part and the blood sampling cartridge.

BEST MODE FOR CARRYING OUT THE INVENTION

The blood test apparatus of the present invention has a housing with an internal cylinder body, and an external cylinder body that covers the internal cylinder body of the housing.

The housing has the internal cylinder body at one end and includes the main members of the blood test apparatus or the main members of the blood test apparatus are attached to the housing. Examples of the main members include: a reciprocating means which moves back and forth inside the internal cylinder body; a blood collection needle which is connected to the reciprocating means; a blood sensor which is attached to the tip part of the internal cylinder body; a measuring circuit to which signals from the blood sensor are supplied; and a negative pressure means which creates a negative pressure inside the external cylinder body.

The external cylinder body is a member that covers the internal cylinder body of the housing and has an opening part in the part where the tip of the internal cylinder body is provided (in the part where the blood sensor is attached). When a blood test is carried out, the opening part of the external cylinder body is pressed against the part to be punctured and plumps the part to be punctured. Therefore, the shape of the opening part of the external cylinder body may be set as appropriate so as to plump the part to be punctured adequately, and, for example, the diameter of the opening part of the external cylinder body may be approximately 10 to 30 mm.

When a blood test is carrying out as described above, the opening part of the external cylinder body is pressed against the part to be punctured. Therefore, the material of the opening part of the external cylinder body is preferably gentle to the skin, and, for example, preferably formed with members with low thermal conductivity. Since resin has lower thermal conductivity than iron and aluminum, resin is preferable for the material of the opening part of the external cylinder.

Figure 1:
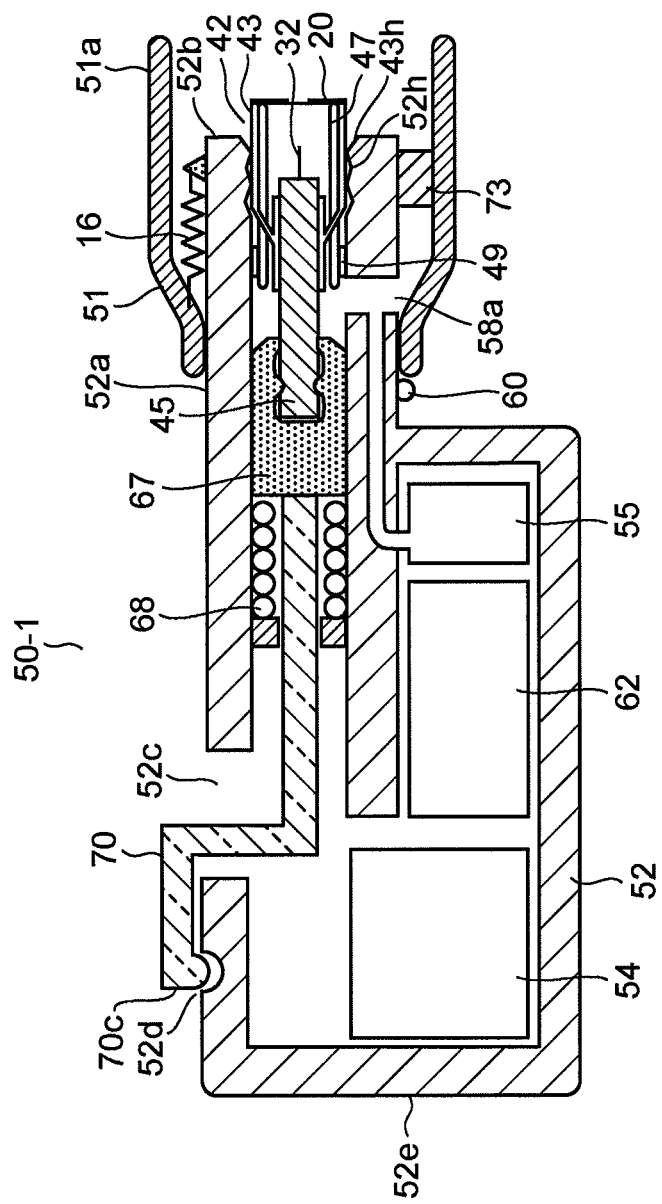
FIG. 1 is a cross-sectional view of the first example of a blood test apparatus.
Figure 2:
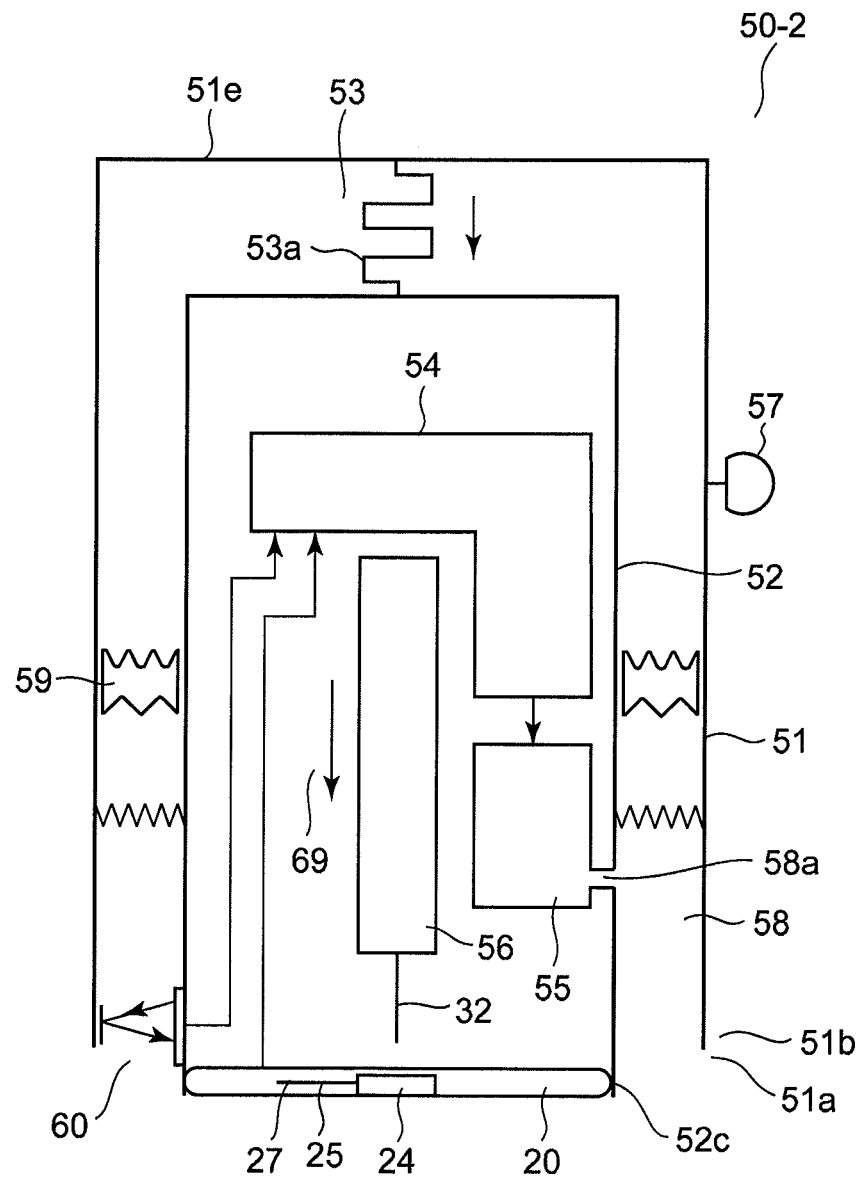
FIG. 2 is a cross-sectional view of the second example of the blood test apparatus.
Figure 3:
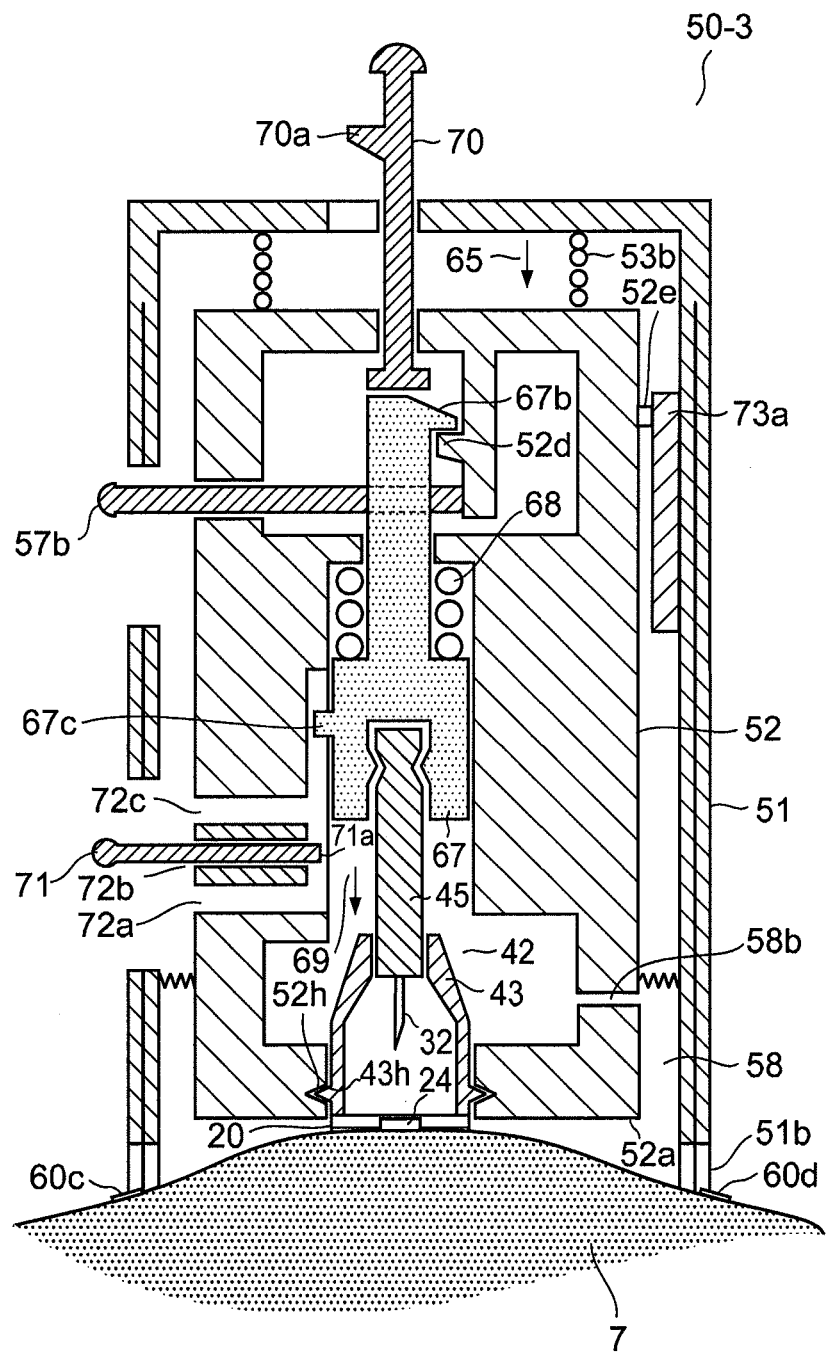
FIG. 3 is a cross-sectional view of the third example of the blood test apparatus.
Figure 5:
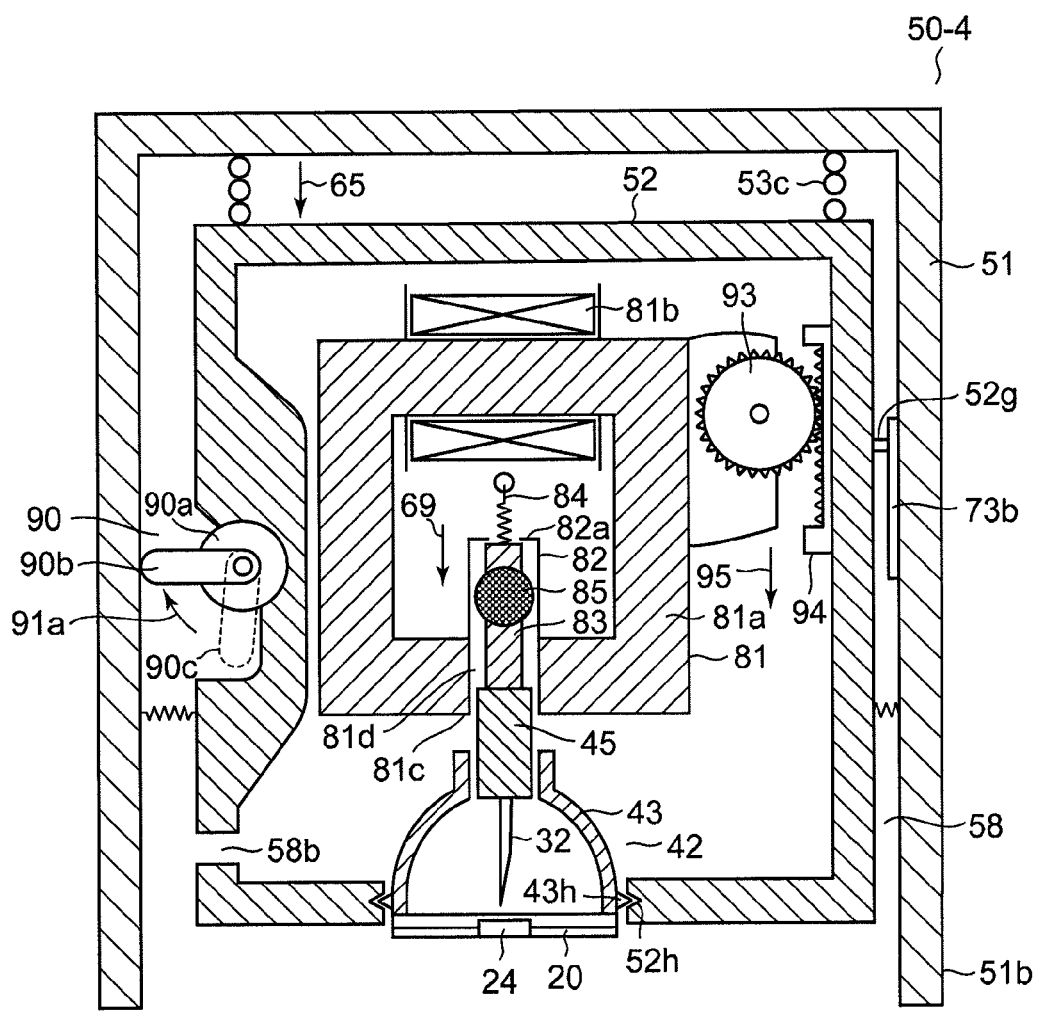
FIG. 5 is a cross-sectional view of the fourth example of the blood test apparatus.

The external cylinder body may cover the internal cylinder body partially (see FIG. 1), or may cover the whole of the housing including the internal cylinder body (see FIGS. 2, 3 and 5). The external cylinder body can be moved relative to the housing. That is, the opening part of the external cylinder body can be in front of or move behind the tip part (part to which the blood sensor is attached) of the internal cylinder body. Further, the external cylinder body is provided so as to return to a predetermined relative position after moving relative to the housing. Therefore, the external cylinder body is preferably connected with the housing via an elastic body such as spring.

The tip of the opening part of the external cylinder body at the initial position (position for moving relative to the housing) may be provided so as to project further from the tip part (part to which the blood sensor is attached) of the internal cylinder body (see FIG. 1) in a tip direction, or, in contrast, may be provided behind the tip part of the internal cylinder body (see FIG. 2).

Further, to make the external cylinder body move smoothly relative to the internal cylinder body, it is also possible to provide a rail in the internal cylinder body (or the external cylinder body) and a tooth that slides on the rail in the external cylinder body (or the internal cylinder body).

The blood test apparatus preferably has: a move detecting sensor (see FIG. 1, for example) that detects a move of the external cylinder body relative to the internal cylinder body; or a skin contact detecting sensor (see FIG. 3, for example) that detects a contact between the opening part of the external cylinder body and the part to be punctured, to start or stop the negative pressure means adequately.

When a blood test is carried out using the blood test apparatus, the external cylinder body is sealed with the part to be punctured. The negative pressure means creates a negative pressure inside the external cylinder body sealed by the part to be punctured, and thereby the part to be punctured is plumped. The plumped part to be punctured is punctured with the blood collection needle connected to the reciprocating means.

As described above, the external cylinder body is sealed by the part to be punctured, and a negative pressure is created inside the external cylinder body. To create a negative pressure in a simple manner, the opening part of the external cylinder body is preferably brought into close contact with the part to be punctured. Therefore, the material of the opening part of the external cylinder body is preferably a soft elastic member (such as rubber).

When the skin is punctured during a blood test, the positions of the external cylinder body and the housing are preferably fixed relative to each other. Therefore, the blood test apparatus of the present invention preferably has the first fixing means for fixing the relative position between the external cylinder body and the housing. The position may be fixed by, for example, pressing a friction member provided on the outer wall of the housing (including the internal cylinder body) against the inner wall of the external cylinder body (see FIG. 3) or by pressing a cam against the inner wall of the external cylinder body (see FIG. 5).

The blood test apparatus of the present invention will be described below with reference to the drawings.

[A First Example of the Blood Test Apparatus]

FIG. 1 shows a cross-sectional view of a first example of the blood test apparatus (blood test apparatus 50-1). Blood test apparatus 50-1 has housing 52 forming a chassis. The material of housing 52 is preferably resin. At one side of housing 52, cylinder-shaped internal cylinder body 52a is formed. Blood sampling cartridge 42 is inserted into end 52b of internal cylinder body 52a. When blood sampling cartridge 42 is inserted into internal cylinder body 52a, positioning concave part 52h provided on the internal cylinder body 52a side and positioning convex part 43h provided in holder 43 of blood sampling cartridge 42 are engaged, and blood sampling cartridge 42 is fixed at a predetermined position within the internal cylinder body 52a (a position in the horizontal direction in FIG. 1).

Blood sampling cartridge 42 preferably has: cylinder-shaped holder 43; blood sensor 20 that is attached to one end of holder 43; lancet 45 that is provided slidably in holder 43; and blood collection needle 32 that is attached to the other end of lancet 45. A plurality of connectors 47 provided in blood test apparatus 50-1 contact with blood sensor 20.

A grip part is formed near one end of lancet 45 configuring blood sampling cartridge 42, and this grip part is held by a holding part provided at one end of plunger 67 that can slide inside internal cylinder body 52a. The other end of plunger 67 is connected to one end of handle 70 formed in the shape of a crank, and latch convex part 70c is formed at the other end of handle 70. Handle 70 passes through hole 52c provided in housing 52 and engages with latch concave part 52d and is latched. That is, the second fixing means including latch convex part 70c and latch concave part 52d fixes plunger 67 to housing 52. It is also possible to fix plunger 67 to housing 52 in advance and then attach lancet 45 with blood collection needle 32 (the same applies to blood sampling cartridge 42 including lancet 45) to plunger 67, or it is possible to attach and insert lancet 56 with blood collection needle 32 to plunger 67 in a state where plunger 67 is not fixed to housing 52 and thereby fix plunger 67 to housing 52.

Plunger 67 is urged by spring 68 toward the direction to end 52b. Measuring circuit 54 stored on the other side 52e of housing 52 is connected to terminal 49 that contacts with connectors 47. Terminal 49 formed in internal cylinder body 52a is configured with a plurality of terminals corresponding to the number of connectors 47. Battery 62 that supplies power is connected to measuring circuit 54.

Blood test apparatus 50-1 has cylinder-shaped external cylinder body 51 that covers internal cylinder body 52a. External cylinder body 51 is connected with housing 52 via spring 16 and urged toward the tip part 51a. Further, one end of external cylinder body 51 (the end where the tip of the internal cylinder body is provided; the end where blood sensor 20 is attached) has opening and the other end is closed. External cylinder body 51 is attached so as to slide on the outer surface of internal cylinder body 52a. That is, rail 73 provided at the opening part side of external cylinder body 51 can slide on the surface of internal cylinder body 52a. In this way, external cylinder body 51 can move relative to internal cylinder body 52a of housing 52 and returns to the initial position after moving relative to internal cylinder body 52a.

The material of tip part 51a of external cylinder body 51 is preferably a soft elastic body such as rubber to apply a uniform pressure to the periphery of the part to be punctured and bring tip part 51a into close contact with the periphery of the part to be punctured for a ease of creating a negative pressure inside external cylinder body 51. Further, the material of tip part 51a (for example, resin) has preferably lower thermal conductivity than iron and aluminum to alleviate stimulus when external cylinder body 51 is brought into contact with the skin of the part to be punctured.

Blood test apparatus 50-1 has move detecting sensor 60 that detects a move of external cylinder body 51. Move detecting sensor 60 is, for example, a micro switch. Move detecting sensor 60 detects a move of external cylinder body 51 toward the side 52e of housing 52. A micro switch does not require power supply, so that it is possible to extend the life of battery 62. Move detecting sensor 60 is not limited to a micro switch and may be a photosensor. By using a photosensor, it is possible to reduce the sliding resistance of external cylinder body 51.

Further, by providing two conductors at the tip of tip part 51a of external cylinder body 51 and measuring the resistance between the conductors, it is also possible to detect skin 7 of the part to be punctured when skin 7 of the part to be punctured abuts on the tip of external cylinder body 51 (skin contact detecting sensor). Even if external cylinder body 51 is moved by error, the detecting sensor does not react, so that it is possible to detect the skin reliably when the skin abuts on tip part 51a of external cylinder body 51.

Negative pressure means 55 connected to measuring circuit 54 creates a negative pressure inside external cylinder body 51 and inside blood sensor 20 via negative pressure path 58a.

[A Second Example of the Blood Test Apparatus]

FIG. 2 is a cross-sectional view of a second example of the blood test apparatus (blood test apparatus 50-2). Blood test apparatus 50-2 shown in FIG. 2 has external cylinder body 51 that covers the whole of housing 52. External cylinder body 51 is a chassis in which opening part 51b is formed at one end 51a and the other end 51e is closed. The material of external cylinder body 51 is preferably resin, but is not particularly limited.

External cylinder body 51 is connected with housing 52 provided inside external cylinder body 51 via urging means 53. Examples of the urging means include an elastic body such as spring (including coil spring and leaf spring) and rubber. The repulsive force of a magnet may be used as the urging means. External cylinder body 51 can move relative to housing 52 against a force of the urging means. In other words, housing 52 can slide inside external cylinder body 51 freely. Further, external cylinder body 51 return preferably to the initial relative position again by the urging means after moving relative to housing 52.

One end 52c of housing 52 is provided at the opening part 51b side of external cylinder body 51, and blood sensor 20 is attached to one end 52c. Blood sensor 20 is preferably attached removably. Blood sensor 20 has: blood storing part 24 provided in the center of the lower surface; supply channel 25 communicating with storing part 24; and detecting section 27 provided in supply channel 25. The detail of blood sensor 20 will be described later.

Housing 52 has measuring circuit 54, negative pressure means 55, reciprocating means 56 and blood collection needle 32, inside. Measuring circuit 54 is electrically connected to detecting section 27 of blood sensor 20 and has a function for measuring component (such as the blood sugar level) in blood led to detecting section 27. When puncturing button 57 provided in housing 52 is pressed, reciprocating means 56 moves back and forth and moves toward the direction of storing part 24 of blood sensor 20 or returns inside housing 52 again. Blood collection needle 32 attached to reciprocating means 56 is directed to storing part 24 and moves back and forth in the same way.

Negative pressure means 55 is configured with a diaphragm pump and starts and stops following commands from measuring circuit 54. Negative pressure means 55 is connected to negative pressure chamber 58 via negative pressure path 58a. Negative pressure chamber 58 communicates with the interior of external cylinder body 51 at the opening part 51b side and storing part 24 of blood sensor 20. Therefore, negative pressure means 55 can create a negative pressure inside opening part 51b and inside storing part 24.

First fixing means 59 can fix the relative position between external cylinder body 51 and housing 52.

The material of opening part 51b of external cylinder body 51 is preferably a soft elastic material such as rubber to apply a uniform pressure to the skin, to bring the skin into close contact with opening part 51b and to create a negative pressure to negative pressure chamber 58 inside external cylinder body 51 more easily. Further, the material of opening part 51b (such as resin) has preferably lower thermal conductivity than iron and aluminum to reduce stimulus when external cylinder body 51 abuts on the skin.

Figure 7:
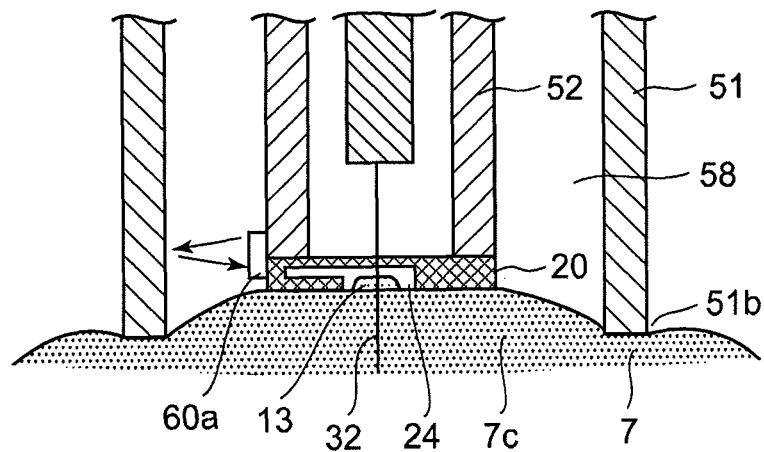
FIG. 7 is a cross-sectional view showing the main part near the punctured part in the blood test apparatus when the skin is punctured.

Move detecting sensor 60 is, for example, reflective photosensor 60a (see FIG. 7). When blood sensor 20 is brought into contact with the skin of the part to be punctured and housing 52 is moved into external cylinder body 51, photosensor 60a detects the move. Photosensor 60a does not contact with external cylinder body 51, and so the sliding resistance between external cylinder body 51 and housing 52 can be reduced. Move detecting sensor 60 is not limited to photosensor 60a and may be micro switch 60b. Microswitch 60b does not require power supply, so that it is possible to extend the life of the battery.

Further, two conductors 60c and 60d (see FIG. 3; blood test apparatus 50-3) provided at opening part 51b of external cylinder body 51 so as to be exposed and used as a skin contact detecting sensor. By measuring the resistance between two conductors 60c and 60d, it is possible to detect a contact between the skin and opening part 51b of external cylinder body 51. When housing 52 moves while the skin does not contacts with opening part 51b of external cylinder body 51, the skin contact detecting sensor does not detect the move, so that it is possible to detect the skin reliably when the skin abuts on opening part 51b.

[A Third Example of the Whole of the Blood Test Apparatus]

FIG. 3 shows a cross-sectional view of a third example of blood test apparatus 50 (blood test apparatus 50-3). The same components as in blood test apparatus 50-2 will be assigned the same reference numerals for ease of explanation.

The reciprocating means of blood test apparatus 50-3 adopts a mechanical method. The "mechanical method" refers to a mechanical driving mechanism that is driven by the elastic force of an elastic body. In blood test apparatus 50-3, housing 52 is provided inside external cylinder body 51. Housing 52 is connected with external cylinder body 51 via spring 53b and urged toward the direction of arrow 65. Therefore, external cylinder body 51 and housing 52 can move relative to each other and return to the predetermined positions after moving relative to each other. Rail 73a formed inside external cylinder body 51 and convex part 52e formed in housing 52 are engaged, and thereby external cylinder body 51 can slide toward the direction of arrow 65 or in the opposite direction.

Plunger 67 is provided inside housing 52 and urged toward the direction of arrow 69 by spring 68. A grip part is formed at one end of plunger 67 and holds a holding part of lancet 45 removably.

Blood collection needle 32 is attached to lancet 45. Further, lancet 45 is provided slidably in holder 43. Blood sensor 20 is attached to one end of holder 43. Holder 43, blood sensor 20, lancet 45 and blood collection needle 32 are preferably integrated to configure blood sampling cartridge 42. Positioning convex part 43h formed in holder 43 and positioning concave part 52h formed in housing 52 are engaged; thereby the position to which cartridge 42 is attached is determined.

The other end of plunger 67 may be pushed out toward the direction of arrow 65 by pushing handle 70. Stopper 70a formed in pushing handle 70 stops handle 70 in external cylinder body 51. That is, the second fixing means is configured with stopper 70a and external cylinder body 51 and fixes the reciprocating means to the external cylinder body. Cartridge 42 is preferably replaced in a state where handle 70 is pushed out toward the direction of arrow 65 and stopped at external cylinder body 51 with stopper 70a, and stopper 70a and external cylinder body 51 are fixed.

Cartridge 42 is inserted into housing 52, and lancet 45 of cartridge 42 is held by plunger 67. By further forcing cartridge 42 into housing 52, spring 68 is contracted and charges energy.

On the other hand, convex part 67b formed at the other side of plunger 67 and convex part 52d formed in housing 52 are latched. In this state, when puncturing handle 57b is pressed, housing 52 is fixed to external cylinder body 51 (see FIG. 4), and then latch of convex part 52d and convex part 67b is released. This mechanism of the first fixing means will be described with reference to FIG. 4.

Figure 4:
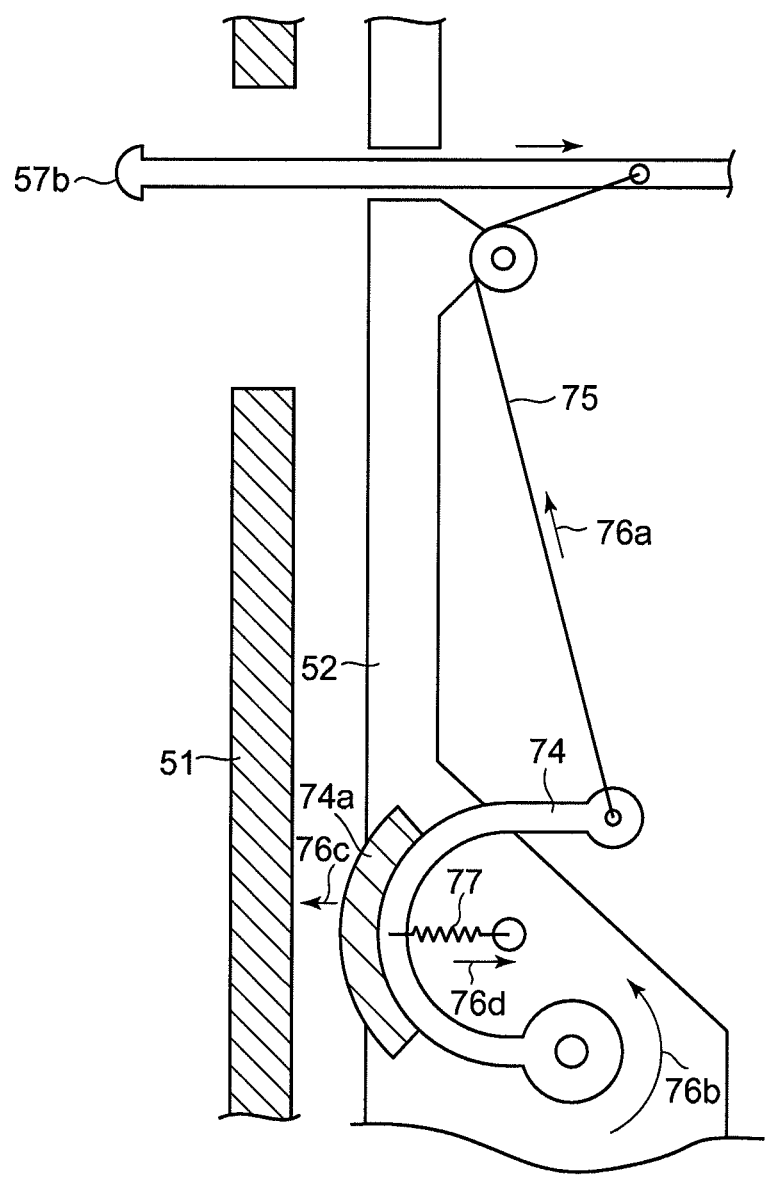
FIG. 4 is a cross-sectional view showing a fixing means of the blood test apparatus in the third example.

FIG. 4 is a cross-sectional view showing the main part of the first fixing means that fixes external cylinder body 51 of blood test apparatus 50-3 and housing 52. In FIG. 4, one side of U-shaped stopping member 74 is fixed at housing 52 rotatably. The other side of stopping member 74 is connected to one side of piano wire 75. The other side of piano wire 75 is fixed at puncturing handle 57b. When puncturing handle 57b is pressed, piano wire 75 is pulled toward the direction of arrow 76a.

When piano wire 75 is pulled toward the direction of arrow 76a, stopping member 74 rotates toward the direction of arrow 76b, and friction member 74a attached on the bottom surface of stopping member 74 moves toward the direction of arrow 76c. Moved friction member 74a is pressed against the inner wall of external cylinder body 51. By the friction resistance between friction member 74a and the inner wall of external cylinder body 51, the relative position between housing 52 and external cylinder body 51 is fixed. Stopping member 74a is urged toward the direction of arrow 76d, and so, when puncturing handle 57b returns to the initial position, stopping member 74 also returns to the initial position and fixing is released.

Plunger 67 in blood test apparatus 50-3 is urged by spring 68 and propelled toward the direction of arrow 69. Blood collection needle 32 breaks through the ceiling of storing part 24 of blood sensor 20 and punctures skin 7.

Blood test apparatus 50-3 has depth adjusting handle 71 that adjusts the puncturing depth of blood collection needle 32. Adjusting handle 71 is inserted into one of puncturing depth adjusting holes 72a, 72b and 72c. Tip 71a of handle 71 inserted to one of the adjusting holes and convex part 67c provided in plunger are engaged, thereby specifying the depth blood collection needle 32 inserting skin 7.

Blood test apparatus 50-3 creates a negative pressure to negative pressure chamber 58 via negative pressure path 58b and further creates a negative pressure inside holder 43 (the upper surface of sensor 20).

Skin contact detecting sensors 60c and 60d formed with conductors are arranged in the opening part of external cylinder body 51. That is, by measuring the electrical resistance between skin contact detecting sensors 60c and 60d, it can be determined whether the tip part of external cylinder body 51 is in contact with skin 7 of the part to be punctured. When contact with skin 7 is detected by skin contact detecting sensors 60c and 60d, negative pressure operation is started. The negative pressure operation is started after skin 7 is in contact with tip part 51b of external cylinder body 51 and seals negative pressure chamber 58, so that the surface of the skin can be sucked in (a negative pressure is created) reliably when necessary, and power supply for driving the negative pressure means is not wasted.

[A Fourth Example of the Blood Test Apparatus]

FIG. 5 is a cross-sectional view showing a fourth example of the blood test apparatus (blood test apparatus 50-4). The reciprocating means of blood test apparatus 50-4 adopts a solenoid operated system. The "solenoid system" refers to the driving mechanism by an electromagnetic force. Housing 52 is provided slidably inside external cylinder body 51 and urged by spring 53c toward the direction of arrow 65.

Electrical magnet 81, which is a ferromagnetic body, held by a rail (not shown) is provided inside housing 52. The cross section of electrical magnet 81 has the shape of "C," and electrical magnet 81 configures core 81a. Core 81a is magnetized by passing a current (applying a current) to coil 81b coiled around core 81a.

Rail 82 is fixed so as to pass through void 81c of core 81a. Plunger 83 that slides on rail 82 is provided. The material of plunger 83 is non-magnetic. One side of plunger 83 is urged by spring 84 toward the opposite direction of arrow 69. Latch part 82a latches plunger 83 so as not to jump from rail 82. Latch part 82a is the second fixing means. As described later, the first fixing means fixes external cylinder body 51 and housing 52 and the second fixing means latches plunger 83, and thereby the positional relationship between external cylinder body 51 and plunger 83 is fixed. The lancet of blood sampling cartridge 42 only has to be inserted to the fixed plunger and held by the plunger.

Figure 6:
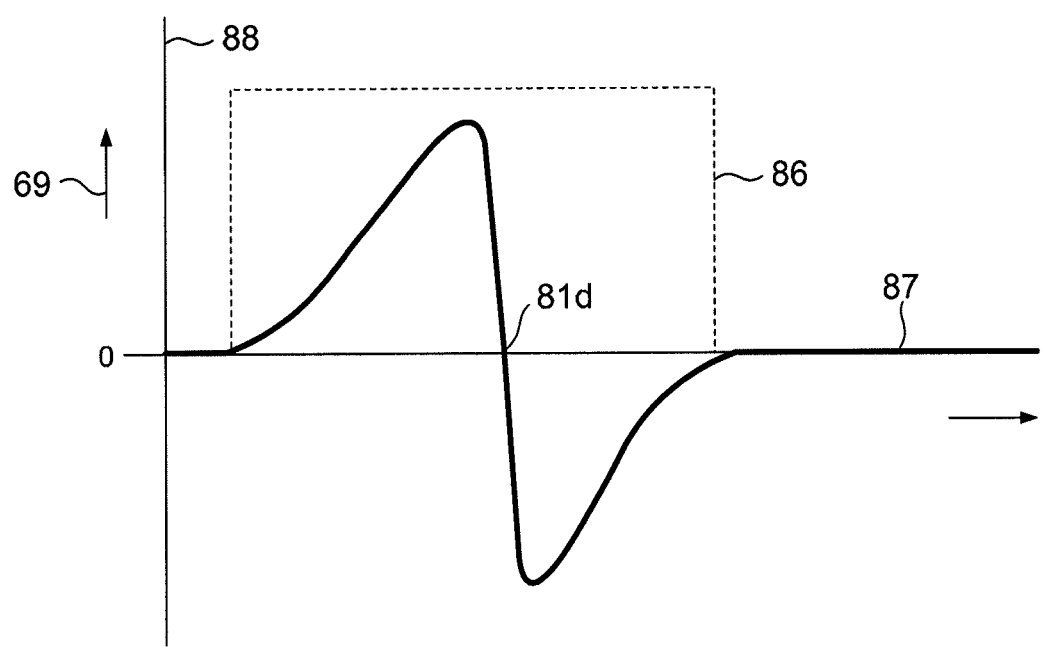
FIG. 6 is a graph showing a force applied to a sphere by a magnetic force of an electrical magnet of the blood test apparatus in the fourth example.

Sphere 85 is embedded in plunger 83, and the material of sphere 85 is ferromagnetic. When the pulse current shown by dotted line 86 in FIG. 6 is applied to coil 81b, electrical magnet 81 is magnetized. Sphere 85 is pulled in by the magnetic force produced, and so plunger 83 is propelled toward the direction of arrow 69 against the force urged by spring 84. In FIG. 6, horizontal axis 87 shows time (msec), and vertical axis 88 shows the direction a force applied to sphere 85. Lancet 45 held by plunger 83 is also propelled toward the direction of arrow 69 with plunger 83. Therefore, blood collection needle 32 attached to lancet 45 breaks through the ceiling of storing part 24 of blood sensor 20 and punctures skin 7.

Sphere 85 which passes through the center 81d of void 81c and is outside core 81, returns to the initial position by being forced toward the opposite direction of arrow 69, and thereby blood collection needle 32 also returns to the initial position. That is, when a pulse current is applied to coil 81b, blood collection needle 32 punctures the part to be punctured and then returns to the initial position.

To apply a strong magnetic force to sphere 85, the magnetic force is preferably concentrated on void 81c. Therefore, the width of void 81c is preferably made narrow, and the width of void 81c is set for example, approximately 10 mm. Further, making the width of void 81c narrow is preferable since narrow width of void reduces leakage of the magnetic force.

When the skin is punctured with blood collection needle 32, housing 52 is fixed to external cylinder body 51 by first fixing means 90. Fixing means 90 is configured with pulse motor 90a and cam 90b attached to the axis of pulse motor 90a. When cam 90b is moved toward the direction of arrow 91a, the relative position between of housing 52 and external cylinder body 51 is fixed. In this state where the relative position is fixed, the part to be punctured is punctured with puncturing needle 32. Further, when cam 90b is rotated in the opposite direction of arrow 91a and set at the position shown by dotted line 90, external cylinder body 51 and housing 52 slide freely. Cam 90b may be controlled using an electrical magnet instead of pulse motor 90a.

Gear 93 attached to electrical magnet 81 is connected to the axis of pulse motor 93a via a velocity reduction mechanism. Further, gear 93 is meshed with teeth 94 provided on the inner wall of housing 52. Therefore, it is possible to control the position of electrical magnet 81 toward the direction of arrow 95 or toward the opposite direction of arrow 95 by controlling pulse motor 93a. That is, by controlling pulse motor 93a, it is possible to adjust the puncturing depth of blood collection needle 32. When cartridge 42 is attached, pulse motor 93a moves electrical magnet 81 closest to the opening part 51b, and latch part 82a latches plunger 83. Further, rail 73b is formed on the inner wall of external cylinder body 51 of blood test apparatus 50-4. Convex part 52g formed on the outer wall of housing 52 engages with rail 73b, and housing 52 can slide toward the direction of arrow 65 or toward the opposite direction of arrow 65.

A blood test using blood test apparatus 50 will be described. First, skin 7 of the part to be punctured (such as a finger) of the patient is brought into contact with blood sensor 20 attached to tip part 52a of housing 52. If blood sensor 20 is in front of external cylinder body 51, blood sensor 20 is forced into the blood test apparatus and skin 7 of the part to be punctured is brought into contact with opening part 51b of external cylinder body 51. On the other hand, when external cylinder body 51 is in front of blood sensor 20, external cylinder body 51 is forced into the blood test apparatus and skin 7 of the part to be punctured is brought into close contact with blood sensor 20.

As a result, as shown in FIG. 7, skin 7 of the part to be punctured (such as a finger) of the patient contacts with opening part 51b of external cylinder body 51, and external cylinder body 51 is sealed with skin 7. Move detecting sensor 60 (for example, photosensor 60a) can detect a move of external cylinder body 51 relative to housing 52, that is, detects a contact between skin 7 and opening part 51b. After detection, negative pressure means 55 starts and creates a negative pressure inside negative pressure chamber 58 and storing part 24.

Figure 8:
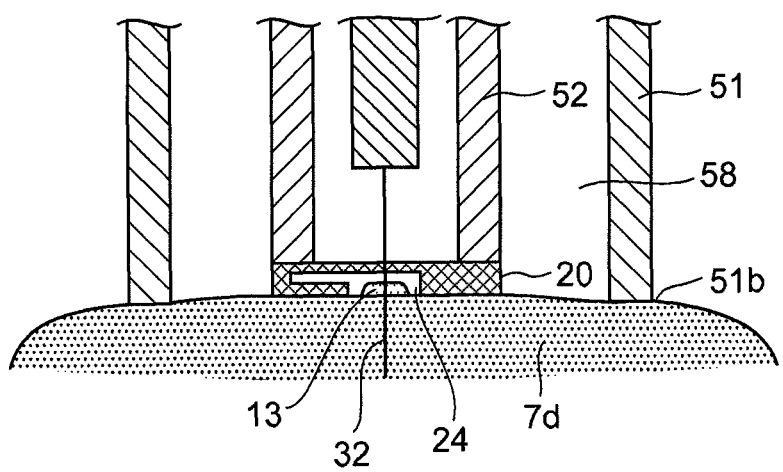
FIG. 8 is a cross-sectional view showing the main part near the punctured part in the blood test apparatus when the skin is punctured.

Even if the level of a negative pressure or the level of a pressure applied by external cylinder body 51 to skin 7 is the same, the amount of plumped skin 7 is varies depending on the hardness of skin 7. That is, if the skin of the part to be punctured is soft, as skin 7c shown in FIG. 7, the skin is plumped significantly. On the other hand, if the skin of the part to be punctured is hard, as skin 7d shown in FIG. 8, the skin is not plumped much.

In this way, the amount of the plumped skin varies depending on the hardness of skin 7 even if the same negative pressure is created. Therefore, it is necessary to adjust the level of the negative pressure appropriately depending on the amount of the plumped skin. Move detecting sensor 60 of blood test apparatus 50 can detect the skin being plumped, so that it is possible to adjust a negative pressure appropriately. Therefore, it is possible to plump the skin adequately by adjusting the level of the negative pressure according to the hardness of skin 7.

If the amount of plumped skin 7 of the part to be punctured is fixed, the volume of storing part 24 of blood sensor 20 becomes fixed, and the depth of puncturing with blood collection needle 32 becomes fixed. Therefore, regardless of condition or nature of skin 7, it is possible to sample blood in approximately the same condition and measure blood correctly.

Figure 9:
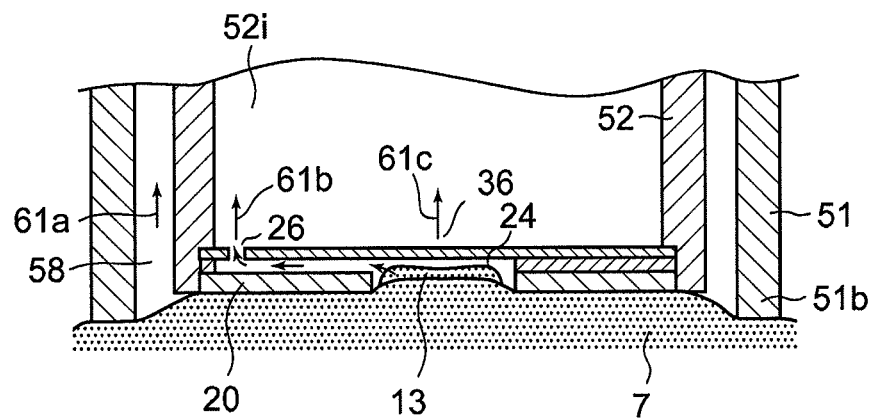
FIG. 9 is a cross-sectional view of the main part near the punctured part in the blood test apparatus and shows a state where blood flowing out from the punctured part is led into the blood sensor.

As shown in FIG. 9, the output of negative pressure means 55 (see FIG. 2) is connected to negative pressure chamber 58 and internal area 52i of the housing (upper part area of blood sensor 20). Therefore, negative pressure means 55 can create a negative pressure to negative pressure chamber 58 and the upper part area of sensor 20.

When negative pressure means 55 operates, the internal part of negative pressure chamber 58 is sucked in as shown by arrow 61a, skin 7 is brought into close contact with blood sensor 20, and the part to be punctured becomes tensed up. At the same time, upper part area 52i of blood sensor 20 is sucked in. By this sucking, the internal part of storing part 24 is sucked in from air hole 26 as shown by arrow 61b and a negative pressure is created inside storing part 24, which caused skin 7 tensed up and puncturing easy. Further, after the skin is punctured with blood collection needle 32, the internal part of storing part 24 is sucked in also from puncturing hole 36 in addition to air hole 26 as shown by arrow 61c. Therefore, a negative pressure is further created inside storing part 24 and sampling of blood 13 to storing part 24 is facilitated.

Blood test apparatus 50 uses air hole 26 and supply channel 25, which are originally used to lead blood to the detecting section by capillary action, also as negative pressure paths.

Therefore, it is possible to create a negative pressure inside storing part 24 without providing a negative pressure path separately. Further, after the puncturing, puncturing hole 36 can be also used as a negative pressure path.

Figure 10:
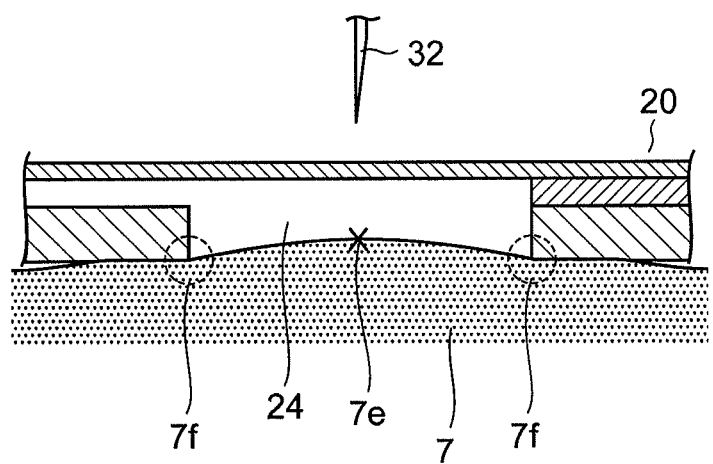
FIG. 10 is a cross-sectional view showing the main part near the part to be punctured in the blood test apparatus before the skin is punctured.

As shown in FIG. 10, blood collection needle 32 is preferably propelled toward the center of storing part 24 and punctures part 7e which is mostly tensed up in skin 7 of the part to be punctured. Further, by puncturing the top part of skin 7, blood 13 can be led into storing part 24 easily. The pressing force of contact point 7f of skin 7 and storing part 24 is the largest, and so, when blood 13 is guided into storing part 24, blood 13 is less likely to flow out from storing part 24.

Prior to the puncturing, the relative position between housing 52 and external cylinder body 51 is fixed by the first fixing means. In a state where the relative positions are fixed, reciprocating means 56 to which blood collection needle 32 is attached, is propelled. Blood collection needle 32 attached to the tip of propelled reciprocating means 56 breaks through the ceiling of storing part 24 of blood sensor 20 (forms puncturing hole 36 in FIG. 9) and punctures skin 7 of the patient.

Blood test apparatus 50 can adjust the amount of the plumped skin to a desired amount, so that it is possible to make the measurement condition fixed regardless of the hardness of the skin. Further, blood test apparatus creates a negative pressure near blood sensor 20 and skin 7 becomes tensed up, so that it is possible to perform puncturing and lead blood into the blood sensor in a simple manner.

Blood 13 flowing out from punctured skin 7 is guided into storing part 24 of blood sensor 20. In addition, blood 13 is also sucked from puncturing hole 36 as shown by arrow 61c, which is facilitating sucking of blood 13. Blood 13 led into storing part 24 is led to detecting section 27 in supply channel 25 and chemically changed by a reagent placed in detecting section 27. The chemical change is converted to an electrical signal by electrodes (described later) of the detecting section and transmitted to measuring circuit 54. Measuring circuit 54 measures the blood sugar level of blood 13. This measurement of blood 13 will be described in detail later.

[The Blood Sensor]

Figure 11:
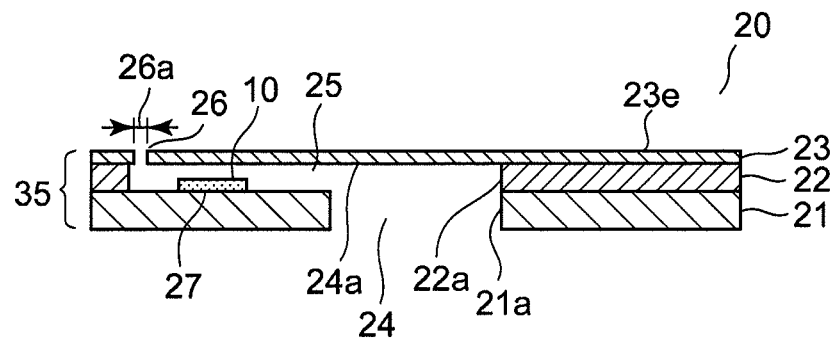
FIG. 11 is a cross-sectional view of the blood sensor.

FIG. 11 is a cross-sectional view showing blood sensor 20, which is one member of blood test apparatus 50. Base plate 35 configuring blood sensor 20 has: substrate 21; spacer 22 pasted on the upper surface of substrate 21; and cover 23 pasted on the upper surface of spacer 22.

Blood storing part 24, which is provided in approximately the center of base plate 35, is formed so as to communicate with hole 21a provided in substrate 21 and hole 22a provided in spacer 22. Storing part 24 opens downward in order to sample blood flowing out from the punctured part. The volume of the storing part is not particularly limited (for example, 0.904 µL).

Detecting section 27 is arranged in supply channel 25, one end of which is connected to storing part 24. The blood stored in storing part 24 flows into supply channel 25 by capillary action and is led to detecting section 27. The volume of supply channel 25 is not particularly limited (for example, 0.144 µL). Further, the other end of supply channel 25 is connected to air hole 26. Diameter 26a of air hole 26 is not particularly limited and may be approximately 50 to 500 µm (for example, 50 µm). By making the diameter of air hole 26 small, blood is prevented from overflowing from air hole 26.

Reagent 10 placed on detecting section 27 is prepared by dropping a reagent solution prepared by adding and dissolving PQQ-GDH (0.1 to 5.0 U/sensor), potassium ferricyanide (10 to 200 mM), maltitol (1 to 50 mM) and taurine (20 to 200 mM) in a 0.01 to 2.0 wt % aqueous solution of CMC on detecting section 27 (see FIG. 11) formed in substrate 21, and drying the reagent solution.

[A First Example of the Blood Sensor]

Figure 12:
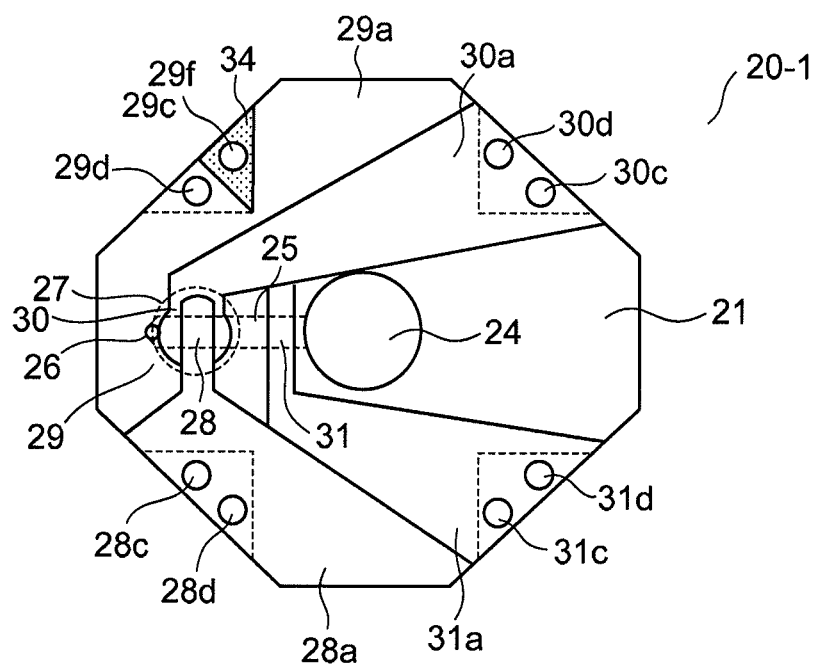
FIG. 12 is a perspective plan view of the first example of the blood sensor.

FIG. 12 is a perspective plan view of a first example of blood sensor 20 (blood sensor 20-1). Although blood sensor 20-1 is an octagon, the shape is not limited, and blood sensor 20-1 may have a shape of an approximate circle. In blood sensor 20-1, detection electrode 31 as an Hct electrode, detection electrode 30 as a counter electrode, detection electrode 28 as an active electrode, detection electrode 30 as a counter electrode and detection electrode 29 as a sensing electrode, are arranged in order from storing part 24 to air hole 26. Detection electrode 28 as an active electrode and detection electrode 30 as a counter electrode configure detecting section 27.

The "active electrode" refers to an electrode for measuring blood components, the "sensing electrode" refers to an electrode for sensing whether blood is supplied to the detecting section, the "counter electrode" refers to a counterpart electrode of the active electrode, and the "Hct electrode" refers to an electrode for measuring the hematocrit level of blood.

Connection electrodes 28a to 31a are derived from detection electrodes 28 to 31 respectively, and connection electrodes 28a to 31a are provided in outer periphery of substrate 21. Contact parts 28c and 28d provided in connection electrode 28a contact with connectors 47a and 47b, respectively. Contact parts 29c and 29d provided in connection electrode 29a contact with connectors 47c and 47d, respectively. Contact parts 30c and 30d provided in connection electrode 30a contact with connectors 47e and 47f, respectively. Contact parts 31c and 31d provided in connection electrode 31a contact with connectors 47g and 47h, respectively. That is, eight connectors 47a to 47h (not shown) contact with blood sensor 20-1 shown in FIG. 12. Further, contact parts 28c and 28d, contact parts 29c and 29d, contact parts 30c and 30d, and contact parts 31c and 31d are preferably arranged near the outer periphery of sensor 20 at regular intervals.

Among the contact parts, contact parts 29c and 29d are electrically insulated each other, but the other contact parts are conductive with each other within pairs. Contact part 29c is formed on insulating member 34 or a slit is provided around contact part 29c, and thereby contact part 29c is electrically insulated from contact part 29d. Contact part 29c can be set as a reference contact part, that is, reference electrode 29f. The "reference electrode" refers to an electrode serving as a reference for identifying the connection electrodes. The reference electrode may be provided in connection electrodes (28a, 30a or 31a) other than connection electrode 29a.

By measuring the insulation resistance between the contact parts within each pair, the contact parts where the insulation resistance is infinite are specified as connection electrode 29a including reference electrode 29f. Connection electrode 30a, connection electrode 31a and connection electrode 28a are specified clockwise from connection electrode 29a. Therefore, when blood sensor 20-1 is attached to the blood test apparatus, even if blood sensor 20-1 is attached to the apparatus without taking into consideration the rotation angle with respect to the axis for attaching the sensor, the connection electrodes can be specified. Therefore, attachment of the blood sensor becomes simple.

[A Second Example of the Blood Sensor]

Figure 13:
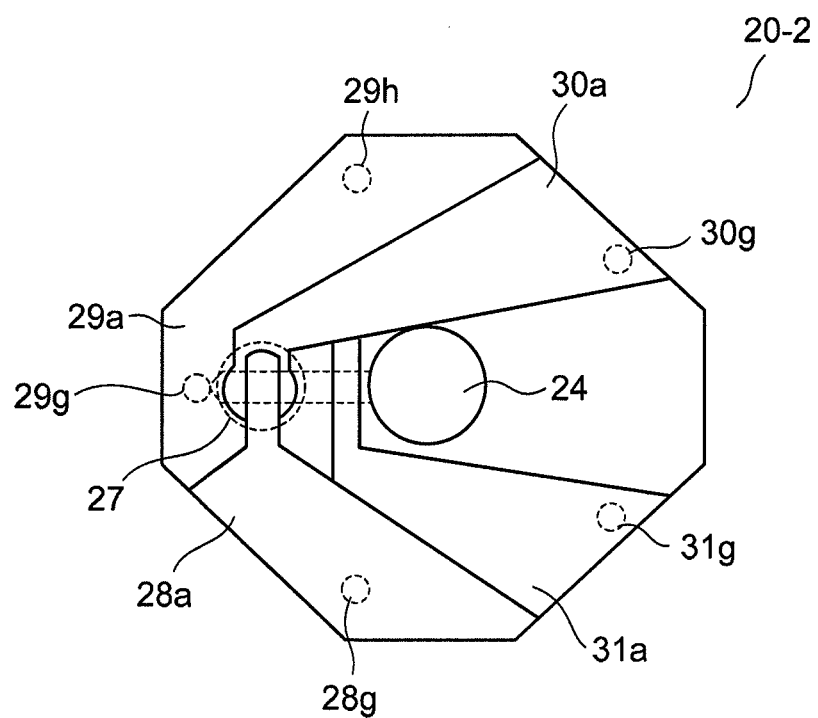
FIG. 13 is a perspective plan view of the second example of the blood sensor.

FIG. 13 is a perspective plan view of a second example of blood sensor 20 (blood sensor 20-2). Blood sensor 20-2 is different from blood sensor 20-1 in the method of specifying a reference electrode, and this difference will be mainly described.

Connection electrodes 28a to 31a of blood sensor 20-2 have contact parts 28g to 31g, respectively. Further, only connection electrode 29a has reference contact part 29h functions as a reference electrode in addition to contact part 29g. The connection electrode which is provided with the reference contact part is not limited to connection electrode 29a and may be any one of connection electrodes 28a to 31a. Contact parts 28g to 31g and reference contact part 29h are preferably arranged near the outer periphery of blood sensor 20-2 at regular intervals.

Blood sensor 20-2 has five contact parts (contact parts 28g to 31g and reference contact part 29h) and the number of connectors connected to the connection electrode is consequently five (47a to 47e). Further, blood test apparatus 50 (including 50-1, 50-2, 50-3 and 50-4) has five terminals 103a to 103e (see FIG. 24) which contact with these connectors 47a to 47e.

The reference contact part 29h can be specified by measuring the electrical resistance between reference contact part 29h and each of contact parts 28g to 31g. That is, the electrical resistance between one of contact parts 28g to 31g and reference contact part 29h becomes zero, so that it is possible to specify reference contact part 29h. Using the specified reference contact part (29h) as a reference, the connection electrodes can be identified clockwise as connection electrode 29a, connection electrode 30a, connection electrode 31a and connection electrode 28a.

In this way, by providing reference contact part 29h, even if blood sensor 20-2 is attached to the blood test apparatus at an arbitrary rotation angle of the blood sensor with respect to the axis for attaching the sensor, the positions of connection electrodes 28a to 31a can be specified automatically. That is, when the blood sensor (or a cartridge with the blood sensor) is attached, it is not necessary to adjust the attaching angle with eyes, so that attaching the blood sensor becomes simple.

[A Third Example of the Blood Sensor]

Figure 14:
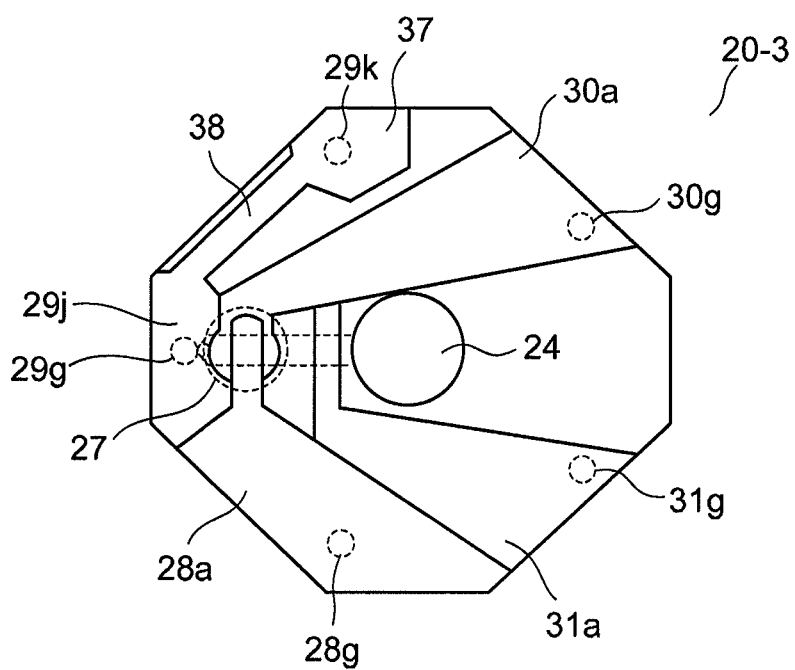
FIG. 14 is a perspective plan view of the third example of the blood sensor.

FIG. 14 is a perspective plan view of a third example of blood sensor 20 (blood sensor 20-3). Blood sensor 20-3 is different from blood sensor 20-2 in that reference electrode 37 is connected with connection electrode 29j via a conductor which has predetermined pattern, and so the difference will be mainly described. Connection electrode 29j is derived from detection electrode 29 (see FIG. 12) and operates in the same way as connection electrode 29a (see FIG. 13) described in blood sensor 20-2.

Reference electrode 37 preferably has reference contact part 29k. Reference contact part 29k and contact parts 28g to 31g are preferably arranged near the outer periphery at regular intervals. More preferably, the contact parts (28g, 29g, 29k, 30g and 31g) may form a regular pentagon. As in blood sensor 20-2, there are five connectors 47 and five terminals 103.

Connection electrode 29j and reference electrode 37 are connected with pattern 38, which is patterned by laser machining. By changing the width of pattern 38, it is possible to adjust the resistance value between contact part 29g and reference contact part 29k to a predetermined value. Reference electrode 37 is used as a reference for specifying the positions of connection electrodes 28a to 31a (in this case, 29a corresponds to 29g) and may be also utilized to identify the product specifications of blood sensor 20-3. For example, it is also possible to measure the blood component by automatically recognizing the calibration curve the blood test apparatus should use by setting the blood test apparatus so that calibration curve 1 is used when the resistance value of pattern 38 is 200 to 1000 ohms, calibration curve 2 is used when the resistance value is 1000 to 2000 ohms, and calibration curve 3 is used when the resistance value is 2000 to 3000 ohms.

By using this resistance value, it is possible to recognize the calibration curve automatically and also identify the product specifications. For example, it is possible to identify which user the product is shipped to, for example, whether the product has the specifications for company A or the specifications for company B. Further, by forming an inductance having various values using pattern 38 and changing the oscillation frequency according to these inductance values, various information can be provided.

By providing reference electrode 37 with reference contact part 29k, when the blood sensor or a cartridge (described later) including the blood sensor is attached to the blood test apparatus, even if the rotation angle with respect to the axis for attaching the sensor is made arbitrary, it is possible to specify connection electrodes 28a to 31a. That is, when the blood sensor or the blood sampling cartridge is attached, the attaching direction does not have to be adjusted with eyes, so that it is possible to attach the blood sensor or the blood sampling in a simple manner.

[An Exploded Plan View of the Blood Sensor]

Figure 15A:
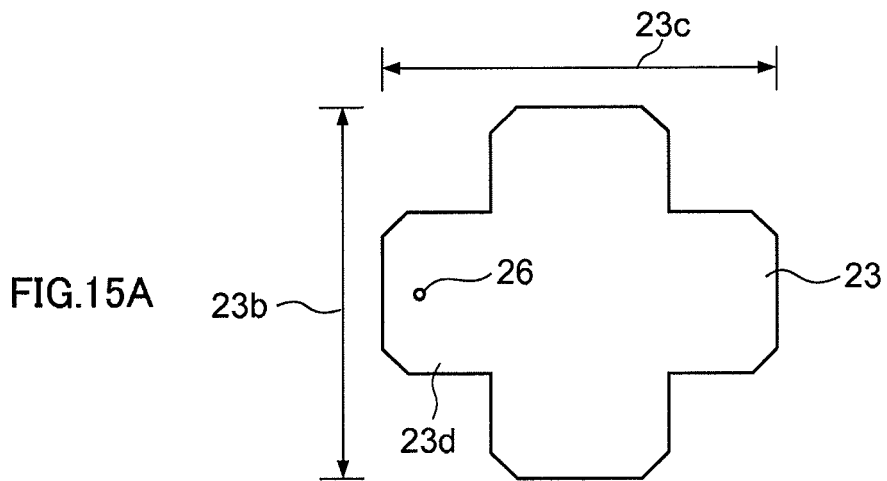
FIG. 15A is a plan view of a cover.
Figure 15B:
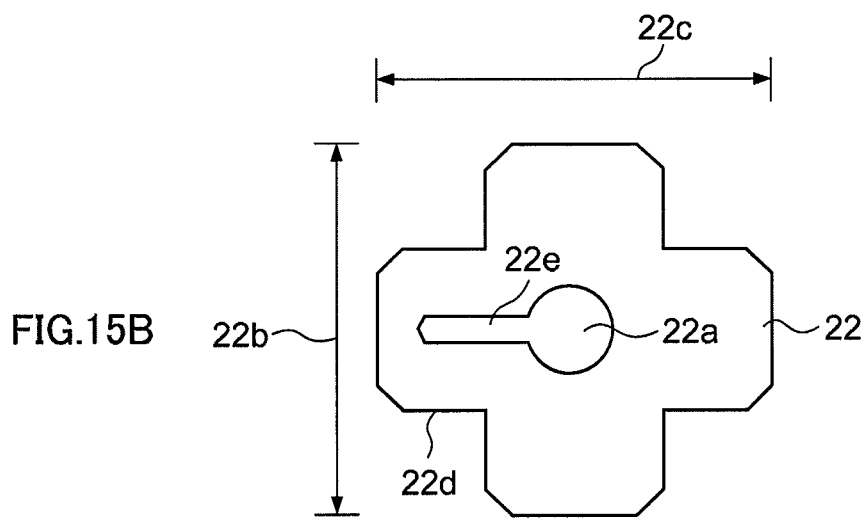
FIG. 15B is a plan view of a spacer.
Figure 15C:
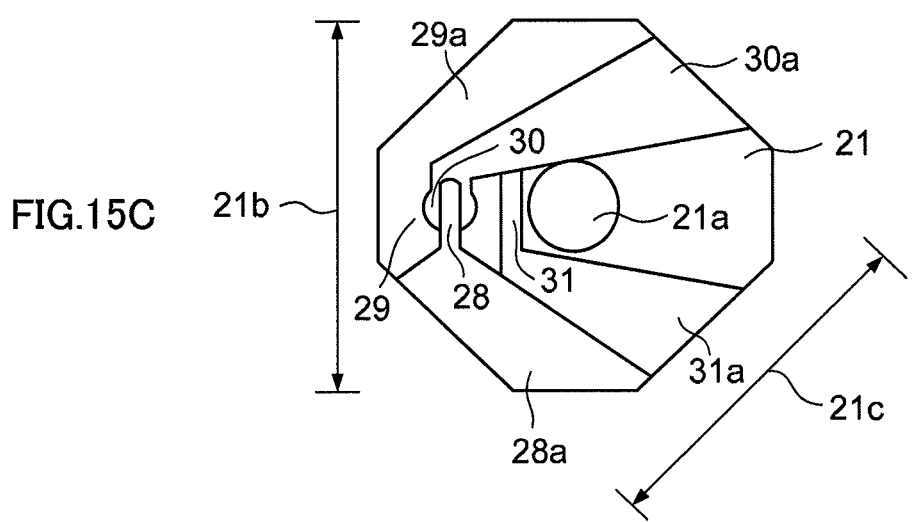
FIG. 15C is a plan view of a substrate.

FIG. 15 is an exploded plan view of blood sensor 20. FIG. 15A shows cover 23 of blood sensor 20, FIG. 15B shows spacer 22 of blood sensor 20, and FIG. 15C shows substrate 21 of blood sensor 20.

FIG. 15C is a plan view of substrate 21 configuring blood sensor 20. Although substrate 21 is an octagon, the shape is not particularly limited. The size of substrate 21 is not particularly limited, and, for example, one dimension 21b may be 9 mm, and the other dimension 21c may be 8 mm. The material of substrate 21 is preferably resin such as polyethylene terephthalate (PET). The thickness of substrate 21 is 0.075 to 0.25 mm, and preferably 0.188 mm.

On the upper surface of substrate 21, detection electrodes 28 to 31, connection electrodes 28a to 31a derived from detection electrodes 28 to 31, respectively, are formed in an integrated manner. These detection electrodes and connection electrodes may be formed by applying laser machining to a conductive layer which is formed using the sputtering method or the vapor deposition method, using gold, platinum and palladium as materials.

Hole 21a is provided in approximately the center of substrate 21. The diameter of hole 21a may be approximately 2 mm. Preferably, the inner wall surface of hole 21a is subjected to weaker hydrophilicity treatment than supply channel 25 or is subjected to weaker water-repellency treatment than upper surface 23e of cover 23.

Hole 21a is preferably formed by being punched out from the side detection electrodes 28 to 31 are formed, using a convex mold so as not to damage the formed electrodes. By this punching, even if a burr is produced in hole 21a by puncturing with the blood collection needle, the burr is formed toward inside storing part 24 (downward in FIG. 16). Therefore, blood is less likely to flow out through hole 21a from storing part 24. This effect of preventing outflow of blood is improved if substrate 21 is subjected to water-repellency treatment.

FIG. 15B is a plan view of spacer 22. Although spacer 22 has an approximate cross shape, the shape is not particularly limited. The size of spacer 22 is also not particularly limited, and, for example, one dimension 22b may be 9 mm and the other dimension 22c may be 8 mm. Hole 22a is provided in approximately the center of spacer 22. Further, hole 22a is provided at the position corresponding to hole 21a which is provided in substrate 21. The diameter of hole 22a is preferably the same as that of hole 21a (approximately 2 mm). Hole 21a and hole 22a configure storing part 24. Preferably, the inner wall surface of hole 22a is subjected to weaker hydrophilicity treatment than supply channel 25 or is subjected to weaker water-repellency treatment than upper surface 23e of cover 23.

Slit 22e is formed in first convex part 22d of cross-shaped spacer from hole 22a, and slit 22e forms blood supply channel 25. The inner wall surface of slit 22e and the area of upper surface of substrate 21 that corresponds to the inner wall surface of slit 22e are subjected to hydrophilicity treatment. Further, the width of slit 22e is 0.600 mm and its length is 2.400 mm, and thereby supply channel 25 with a cavity of 0.144 μL is formed. In this way, test can be performed with a small amount of blood, so that the load of the patient can be alleviated and the test does not make the patient feel fear.

The material of spacer 22 is polyethylene terephthalate, and its thickness may be 0.05 to 0.15 mm (for example, 0.1 mm).

FIG. 15A is a plan view of cover 23. Although cover 23 has an approximate cross shape, the shape is not particularly limited. The size of cover 23 is also not particularly limited, and, for example, one dimension 23b may be 9 mm, and the other dimension 23c may be 8 mm. Air hole 26 is provided in one convex part 23d of cover having cross-shape so as to correspond to the tip part of supply channel 25. Preferably, the diameter of air hole 26 is approximately 50 μm.

The material of cover 23 is preferably resin such as polyethylene terephthalate. The thickness of cover 23 may fall in a range of 0.05 to 0.25 mm, and preferably 0.075 mm.

Upper surface 23e of cover 23 that forms the upper surface of base plate 35 is preferably subjected to water-repellency treatment. On the other hand, the area of the lower surface corresponding to the ceiling surface of supply channel 25 is preferably subjected to hydrophilicity treatment (see FIG. 11). Further, preferably, ceiling surface 24a of storing part 24 is subjected to weaker hydrophilicity treatment than supply channel 25 or is subjected to weaker water-repellency treatment than upper surface 23e of cover 23. More preferably, ceiling surface 24a of storing part 24 is subjected to weaker hydrophilicity treatment than supply channel 25 and is subjected to weaker water-repellency treatment than upper surface 23e of cover 23 (see FIG. 11).

To improve the hydrophilicity or water-repellency, hydrophilic material or water-repellent material may be mixed in the material of the members forming the blood sensor or apply hydrophilic material or water-repellent material to the surface of the members. By adjusting the amount of the hydrophilic material or water-repellent material to be mixed or applied, the level of hydrophilicity or water-repellency is also adjusted. Further, by dissolving or removing hydrophilic material from hydrophobic material (plastic, for example, polyethylene terephthalate) with the hydrophilic material applied on the surface, the hydrophilicity can be reduced. Still further, the characteristic of the hydrophilic material can be adjusted by radiating UV to the hydrophilic material.

Blood sensor 20 is manufactured by, for example, the following method. Water-repellency treatment is applied to upper surface 23e of cover 23 in advance. Further, hydrophilicity treatment is applied to the whole surface of the lower surface of cover 23, which is the ceiling surface of supply channel 25. Next, substrate 21, spacer 22 and cover 23 are pasted. After substrate 21, spacer 22 and cover 23 are pasted, the hydrophilic material of upper surface 24e may be dissolved and removed by radiating short-wavelength UV from the opening of storing part 24.

The thickness of substrate 21, spacer 22 and cover 23 of blood sensor 20 and their ratio are important for sampling blood. First, to cause capillary action in supply channel 25, the thickness of spacer 22 preferably falls within a range of 0.05 to 0.15 mm (preferably 0.1 mm).

Further, to adjust the volume of storing part 24 and the volume of supply channel 25, it is necessary to adjust the thickness of spacer 22 and the thickness of substrate 21. The thickness of substrate 21 is preferably the same as the thickness of spacer 22 or greater and preferably falls within the range where the thickness of substrate 21:the thickness of spacer 22=1:1 to 5:1 (preferably, 2.5:1). Further, cover 23 is preferably thinner than substrate 21 so that the total thickness of blood sensor 20 becomes small. Therefore, the thickness of substrate 21:the thickness of spacer 22:the thickness of cover 23 may be 2.5:1.3:1 as a reference.

Figure 16:
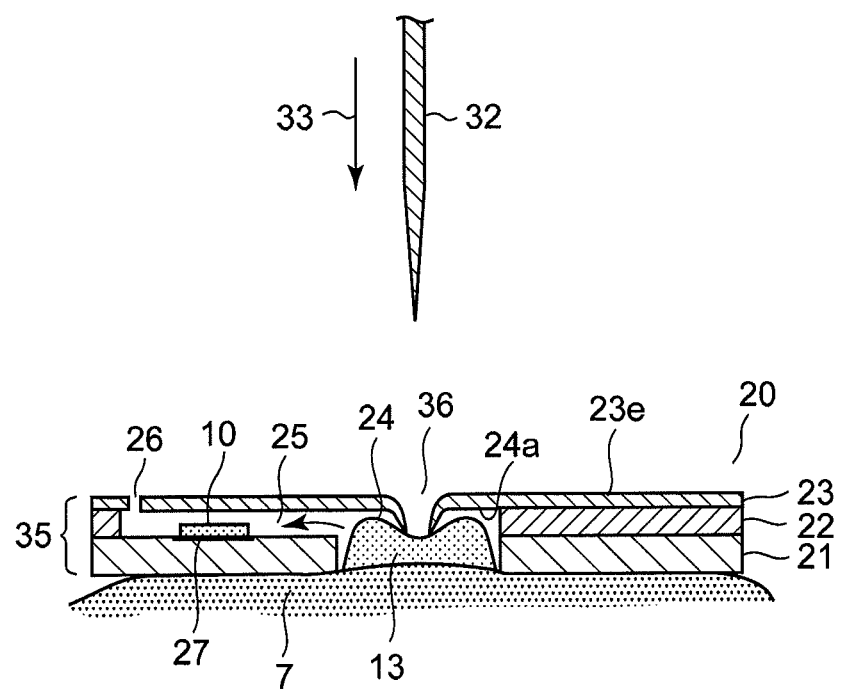
FIG. 16 illustrates the blood sensor and the operation of the blood collection needle.

The relationship between blood sensor 20 and blood collection needle 32 upon blood sampling will be described. As shown in FIG. 16, first, blood sensor 20 is brought into contact with skin 7 of the part to be punctured (such as a finger) of the patient. Blood collection needle 32 is then propelled toward the direction of arrow 33. Propelled needle 32 breaks through cover 23 configuring ceiling surface 24a of storing part 24 to form puncturing hole 36 in cover 23. Further, blood collection needle 32 makes a scar on skin 7 via puncturing hole 36. Blood 13 flowing out from the scar fills storing part 24.

Blood 13 that fills storing part 24 is prevented from flowing out from puncturing hole 36 that is subjected to water-repellency treatment. Further, supply channel 25 is subjected to hydrophilicity treatment, and the side surface and ceiling surface 24a of storing part 24 are subjected to weaker hydrophilicity treatment than supply channel 25 or subjected to weaker water-repellency treatment than upper surface 23e of cover 23, so that blood 13 reaches entrance of supply channel 25 after filling storing part 24, flows into supply channel 25 by capillary action, and flows into detecting section 27 in a rate controlling state (at a constant speed).

Next, the relationship between air hole 26 and puncturing hole 36 will be described. The area of air hole 26 of blood sensor 20 is preferably smaller than the area of puncturing hole 36 formed by blood collection needle 32 to make the resistance to the outflow of blood from puncturing hole 36 smaller than the resistance to the outflow of blood 13 from air hole 26 by making the area of air hole 26 larger than the area of puncturing hole 36. By this means, most of blood 13 sampled more than necessary flows out from puncturing hole 36, and the amount of blood 13 flowing out from air hole 26 becomes extremely small. Therefore, blood 13 does not wash away reagent 10 and reacts with reagent 10 sufficiently in detecting section 27, so that it is possible to realize a correct test. The diameter of air hole 26 may be 50 to 500 μm (for example, 50 μm). Further, preferably, the diameter of air hole 26 is smaller than the diameter of blood collection needle 32 and the diameter of air hole 26 is approximately 10 to 80% of the diameter of blood collection needle 32, and, more preferably, approximately half of the diameter of blood collection needle 32.

Water-repellency treatment is applied to upper surface 23e of cover 23 of blood sensor 20, so that blood 13 is prevented from flowing out from air hole 26 and puncturing hole 36. Therefore, it is not necessary to sample blood 13 wastefully, and the load on the patient is alleviated. Further, the inner wall of storing part 24 of blood sensor 20 is subjected to weaker hydrophilicity treatment than the inner wall of supply channel 25 or is subjected to weaker water-repellency treatment than upper surface 23e, so that blood 13 stored in storing part 24 flows into supply channel 25 in a rate controlling state and led to detecting section 27. Therefore, the melting behavior of reagent 10 exhibits no variation, and the component of blood 13 can be measured correctly.

Blood sensor 20 has blood storing part 24 and blood supply channel 25, and the volume of blood storing part 24 is one to twenty times, preferably four to fifteen times, and, more preferably, five to seven times as much as the volume of blood supply channel 25. For example, the volume of blood storing part 24 may be 0.904 μL, and the volume of blood supply channel 25 may be 0.144 μL. By controlling the volume ratio between blood storing part 24 and blood supply channel 25 adequately, the speed of blood flowing in the supply channel can be controlled constant and the flow rate of blood flowing in the supply channel can be controlled adequately, so that blood does not wash away reagent 10 and reacts with reagent 10 sufficiently, which realizes a correct test.

Further, by controlling the volume ratio between blood storing part 24 and blood supply channel 25, it is possible to reduce their volumes. Therefore, the amount of blood sampled for a test can be reduced, and the load on the patient can be also reduced.

[The Blood Sampling Cartridge]

Blood sensor 20 of blood test apparatus 50 of the present invention is preferably integrated with holder 43 and configures blood sampling cartridge 42. Blood sampling cartridge 42 is inserted into internal cylinder body 52a of housing 52.

Figure 17:
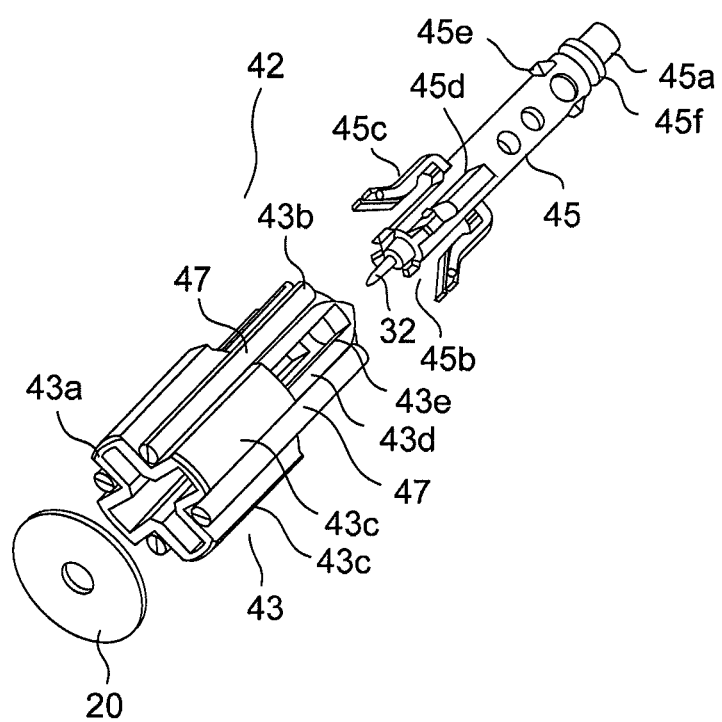
FIG. 17 is a diagrammatic perspective assembly view of the blood sampling cartridge.

FIG. 17 is a diagrammatic perspective assembly view of cartridge 42. In FIG. 17, sensor 20 that examines sampled blood 13 is attached to one end 43a of holder 43. The outer surface of holder 43 has the shape of a cross, and connectors 47 (provided on the blood test apparatus 50 side) formed with conductive metal are led between cross-shaped convex parts 43c. The other end of holder 43 has another convex parts 43d formed integrated with convex parts 43c, and convex parts 43d have holes 43e.

Lancet 45 is inserted into holder 43. Guides 45c for preventing reuse, are provided 180 degrees apart from each other and provided integrated with lancet 45. Guides 45d for improving linear mobility are provided between guides 45c 180 degrees apart from each other. Guide 45d can slide inside hole 43e. Grip part 45f is provided between convex parts 45e provided near one end 45a of lancet 45, and one end 45a.

Figure 18A:
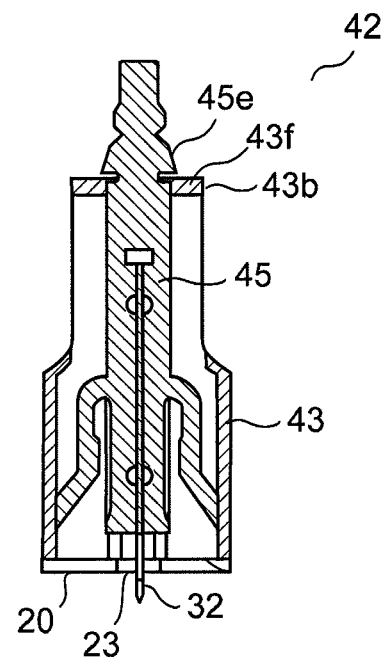
FIG. 18A is a cross-sectional view of the blood sampling cartridge when the skin is punctured.

FIG. 18A is a cross-sectional view of cartridge 42 upon puncturing. In this state, blood collection needle 32 breaks through cover 23 configuring blood sensor 20 and stays. Convex part 45e of lancet 45 is latched at latch part 43f provided at the other end 43b of holder 43, and so blood collection needle 32 does not further project from blood sensor 20.

Figure 18B:
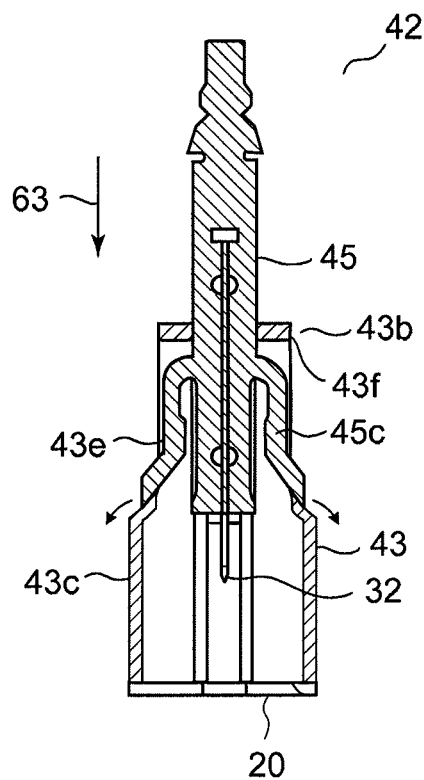
FIG. 18B is a cross-sectional view of the blood sampling cartridge after the skin is punctured.

FIG. 18B is a cross-sectional view of cartridge 42 after puncturing is finished. In this state, blood collection needle 32 is accommodated in holder 43 and stays. The base of guide 45c of lancet 45 is stopped at latch part 43f and thereby lancet 45 stays. Therefore, lancet 45 does not fall off from holder 43.

In the state in FIG. 18B, cartridge 42 is removed from housing 52 of blood test apparatus 50. Even if lancet 45 of removed cartridge 42 is pushed toward the direction of arrow 63, guide 45c runs onto convex parts 43c through hole 43e of holder 43. The base of guide 45c is engaged with the end of hole 43e and stay. Therefore, blood collection needle 32 does not project from sensor 20 again and is secure and does not make the patient feel fear.

Figure 19:
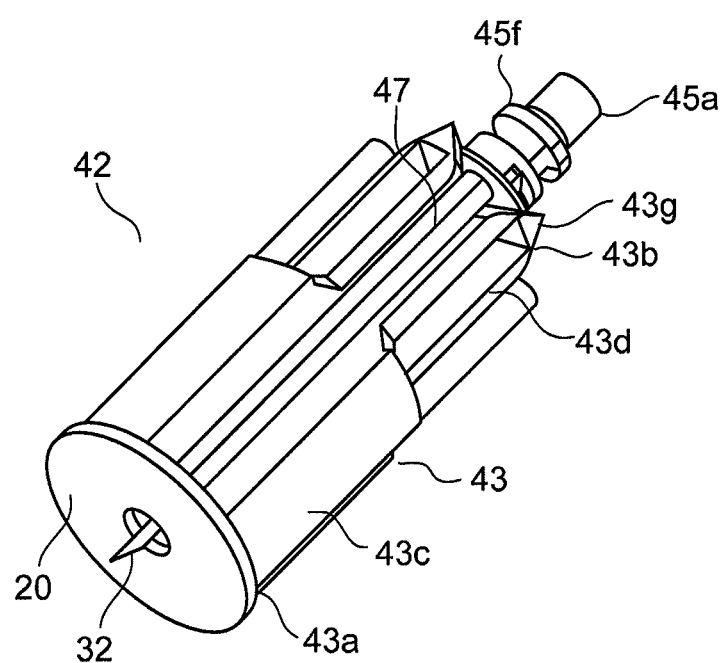
FIG. 19 is a diagrammatic perspective view of the blood sampling cartridge.

FIG. 19 is a diagrammatic perspective view of cartridge 42. As shown in FIG. 19, the height of convex part 43c formed at the one end 43a side is greater than the height of convex part 43d formed at the other end 43b side. That is, the convex part 43d side of holder 43 is thinner than the convex part 43c side, which makes insertion of cartridge 42 into housing 52 of blood test apparatus 50 easily. Further, tip part 43g having a sharp angle and projecting toward tip 43b is formed at convex part 43d.

The whole of cartridge 42 is inserted into and removed from housing 52, and so blood collection needle 32 and blood sensor 20 is freely attached to and removed from housing 52 together. Therefore, blood sensor 20 and blood collection needle 32 can be attached and replaced in a simple manner.

Figure 20:
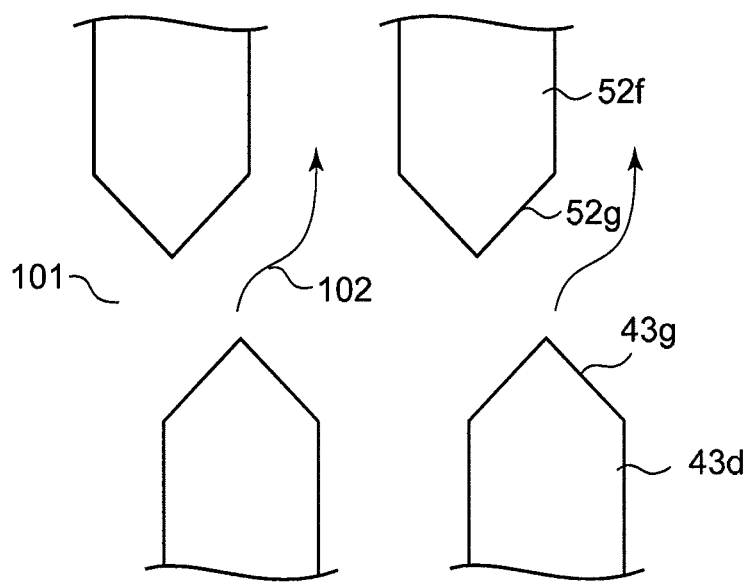
FIG. 20 is a cross-sectional view showing the main part of the attaching guide part of the attaching part.

FIG. 20 is a developed plan view of the main part of guide part 101 that helps inserting cartridge 42 into housing 52. Convex part 43d is formed in holder 43, and convex part 52f is formed inside cylinder-shaped housing 52. Tip part 52g of convex part 52f and tip part 43g of convex part 43d face each other and have a sharp angle. Convex part 52f and its tip part 52g, and convex part 43d and its tip part 43g configure guide part 101.

When cartridge 42 is inserted into housing 52, even if the relative position between housing 52 and holder 43 is shifted, cartridge 42 is inserted along guide part 101 as shown by arrow 102 while the course of cartridge 42 is corrected. Therefore, connectors 47 provided in cartridge 42 contact with terminals 103 provided in housing 52 reliably.

Figure 21:
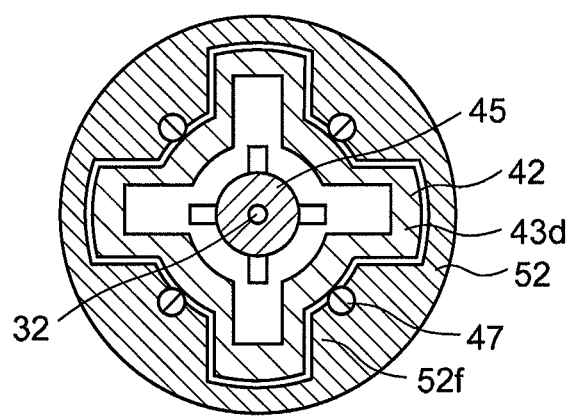
FIG. 21 is a cross-sectional view showing a state where the blood sampling cartridge is attached to the attaching part.

FIG. 21 is a cross-sectional view showing a state where cartridge 42 is inserted into housing 52. As shown in FIG. 21, cartridge 42 is inserted along guide part 101, then convex part 52f and convex part 43d are engaged, so that the angle of cartridge 42 with respect to housing 52 is modified to a predetermined angle (an angle that makes connectors 47 abut on terminals 103), and cartridge 42 is fixed. As a result, signals of blood sensor 20 are delivered to measuring circuit 54 reliably.

Figure 22A:
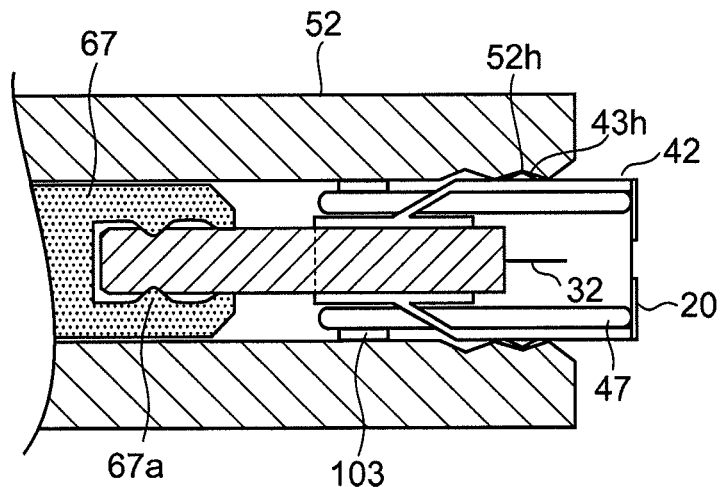
FIG. 22A shows a state before the skin is punctured.

FIG. 22 is a cross-sectional view of cartridge 42 and housing 52 into which cartridge 42 is inserted. FIG. 22A shows a state before puncturing. Plunger 67 is pulled backward, and blood collection needle 32 is arranged inside cartridge 42. Positioning concave part 52h is formed inside housing 52, and positioning convex part 43h is formed outside holder 43. Positioning convex part 43h engages with positioning concave part 52h, and thereby cartridge 42 is fixed to housing 52. Further, sensor 20 and terminals 103 are electrically connected via connectors 47. Terminals 103 are connected to measuring circuit 54.

Figure 22B:
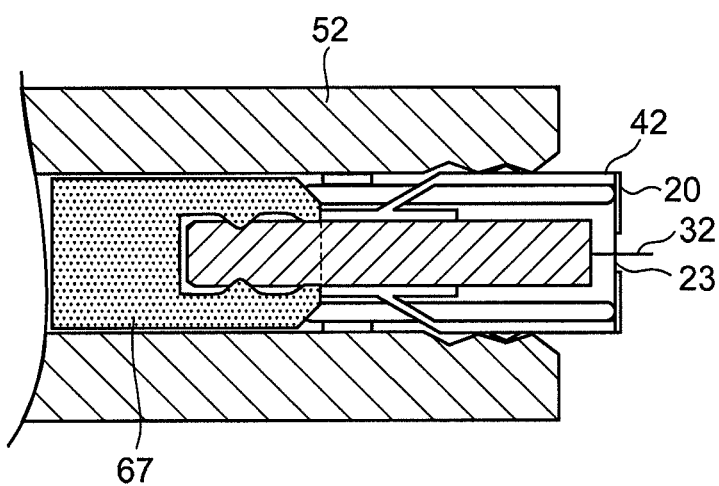
FIG. 22B shows a state where the skin is punctured.

FIG. 22B shows a state upon puncturing. Plunger 67 projects forward, and blood collection needle 32 projects through cover 23 of blood sensor 20.

Figure 22C:
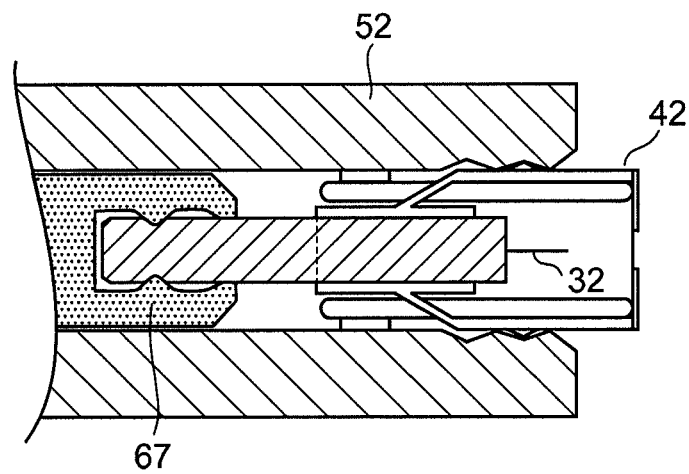
FIG. 22C shows a state after the skin is punctured.

FIG. 22C shows a state after puncturing. Plunger 67 is pulled backward, and blood collection needle 32 is accommodated in cartridge 42. In this way, except for the state where plunger 67 projects forward, blood collection needle 32 is accommodated inside cartridge 42.

[The Flow of the Blood Test]

Figure 23:
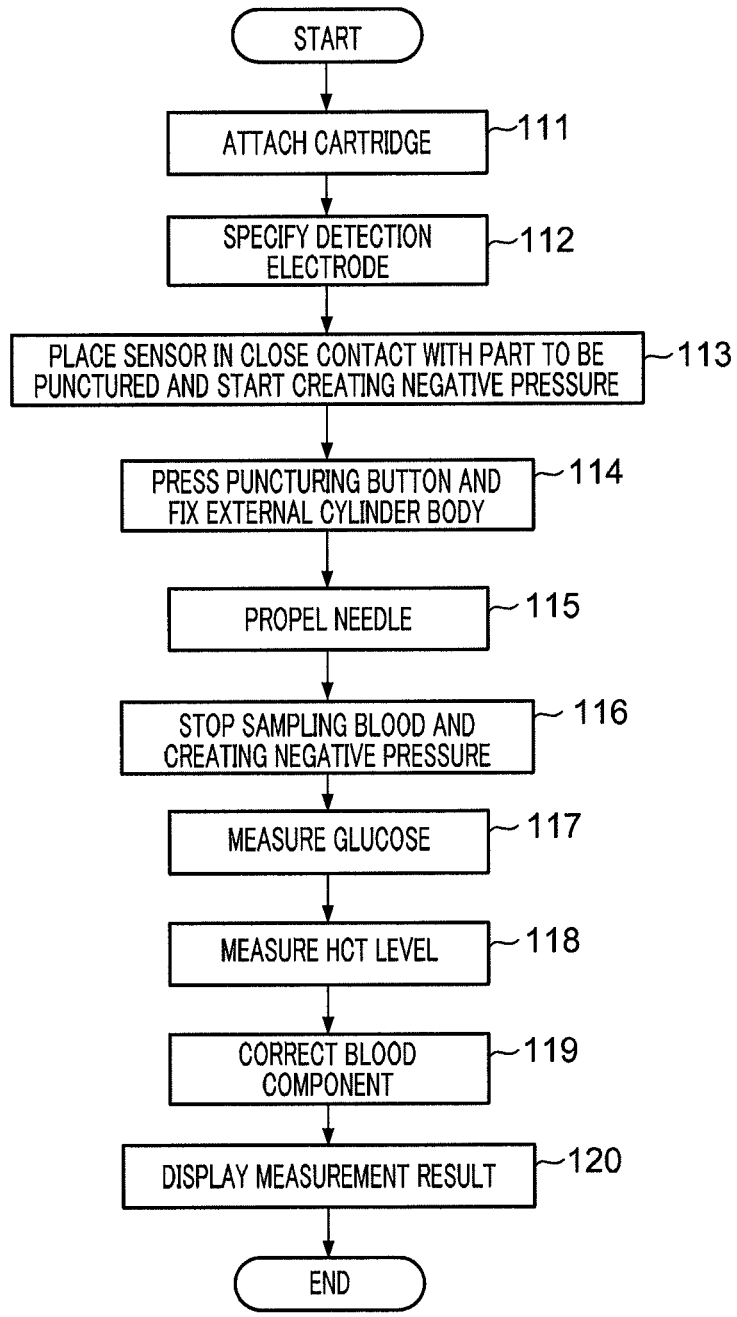
FIG. 23 shows a flow of a test using the blood test apparatus.

A flow of a blood test using blood test apparatus 50 will be described with reference to FIG. 23. First, attaching step 111 of cartridge 42 to blood test apparatus 50 will be described. In attaching step 111, plunger 67 is fixed to external cylinder body 51 or housing 52 by the second fixing means. When cartridge 42 is inserted into housing 52, holder 43 is pressed into housing 52 and latched, and positioning concave part 52h and positioning convex part 43h are engaged each other to determine the position. Further, grip part 45f of lancet 45 is held by holding part 67a of plunger 67.

Next, in step 112, connection electrodes 28a to 31a of blood sensor 20 are specified. For example, in the case of blood sensor 20-1 (see FIG. 12), the resistance values between each of contact parts 28c to 31c and each of contact parts 28d to 31d, are measured by measuring circuit 54, and reference electrode 29f is specified. Using reference electrode 29f as a reference, connection electrodes 29a, 30a, 31a and 28a are specified clockwise. In step 112, connection electrodes 28a to 31a of blood sensor 20 attached to the blood test apparatus at an arbitrary angle are specified, and functions of the detection electrodes are specified.

In step 113, blood sensor 20 of blood sampling cartridge 42 is pressed against skin 7 of the part to be punctured of the patient and brought into close contact with the part to be punctured. By this means, housing 52 is pressed, and the position relative to external cylinder body 51 changes. When move detecting sensor 60 detects this change, negative pressure means 55 starts. It is possible to measure a predetermined time since a negative pressure is created by timer 129 and display on display section 125 that puncturing is possible, after the predetermined time.

In step 114, puncturing button 57 is pressed. Signals from puncturing button 57 are recognized by measuring circuit 54, and the first fixing means (for example, friction member 74a shown in FIG. 4 and fixing means 90 shown in FIG. 5) operates, and thereby external cylinder body 51 is fixed to housing 52.

In step 115, blood collection needle 32 attached to lancet 45 which is connected with the plunger, is propelled toward skin 7 of the part to be punctured. To be more specific, for example, in blood test apparatus 50-1, latch of concave part 52d of housing 52 and convex part 70c of handle 70 is released, in blood test apparatus 50-3, the locking mechanism configured with convex part 67b of plunger 67 and convex part 52d of housing 52 is released, and in blood test apparatus 50-4, a pulse current shown by dotted line 86 is outputted to coil 81b of electrical magnet 81.

In step 116, blood collection needle 32 punctures the part to be punctured, and blood 13 flows out from skin 7 of the punctured part. The outflowing blood 13 is stored in storing part 24 inside sensor 20. Blood 13 further flows into supply channel 25 by capillary action and is led to detecting section 27. When blood 13 led to detecting section 27 reaches detection electrode 29 as a sensing electrode, detection electrode 29 determines that the amount of blood 13 required for measurement is obtained. At that point, the operation of negative pressure means 55 is stopped, and a negative pressure is released. It is also possible to stop negative pressure means 55 when move detecting sensor 60 detects a change in the relative position between the external cylinder body and the housing.

After stopping supplying a negative pressure, extra blood is not sampled, and so the load on the patient can be alleviated significantly. When blood 13 is not detected at detecting section 27 after a predetermined time has passed or when the amount of blood 13 is not adequate (the amount can be detected from the resistance between detection electrode 28 and detection electrode 29), a warning means may warn the patient, or the measure may be displayed on display section 125.

In measuring step 117, the glucose content is measured. The glucose in blood and a glucose oxidation-reduction enzyme are reacted for a certain period. After the reaction, a voltage is applied between detection electrode 28 as an active electrode and detection electrode 30 as a counter electrode. The mediator in a reduction condition, produced on the active electrode by enzyme reaction, is oxidized, and the glucose content is measured by measuring its oxidation current.

In step 118, the hematocrit (Hct) level is measured. A voltage is applied between detection electrode 31 as an active electrode and detection electrode 28 as a counter electrode. A current depending on the Hct level is measured, and the Hct level (hematocrit level) is measured based on this current.

In step 119, the blood component value (glucose content) is corrected. That is, using the Hct level measured in step 118, the glucose content calculated in step 117 is corrected. In step 120, the corrected value is displayed on display section 125 (see FIG. 24). Used cartridge 24 after measurement is finished is replaced every measurement.

Figure 24:
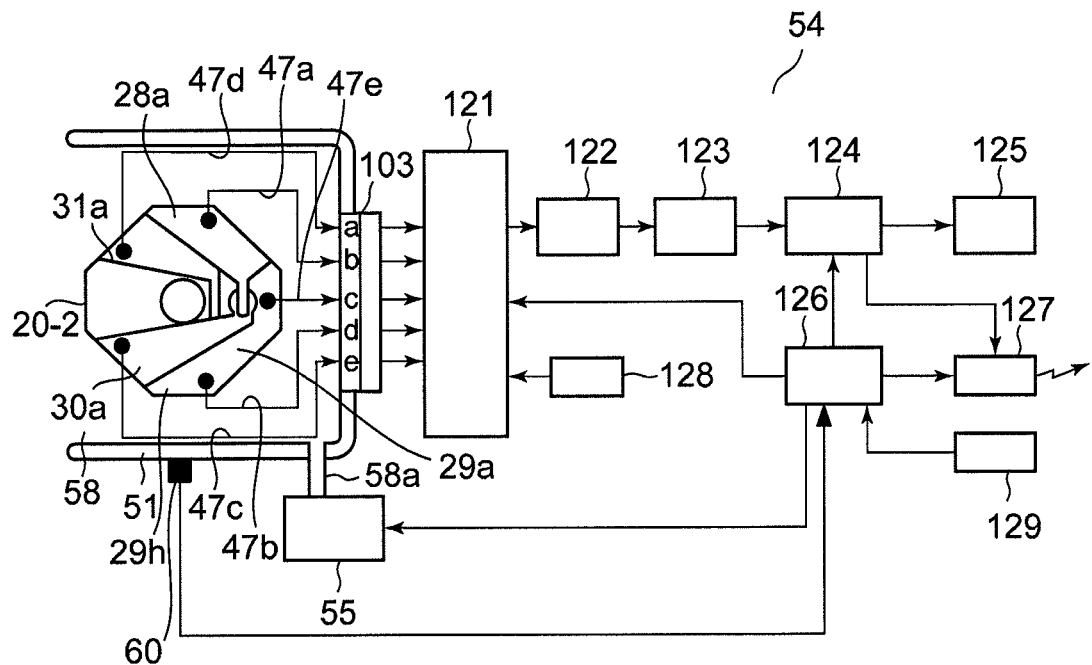
FIG. 24 is a block diagram of the blood test apparatus.
Figure 25:
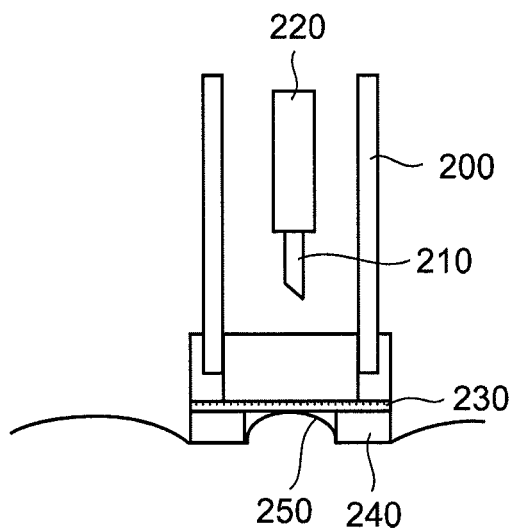
FIG. 25 is a cross-sectional view showing the vicinity of the sensor of the conventional blood test apparatus.
Figure 26:
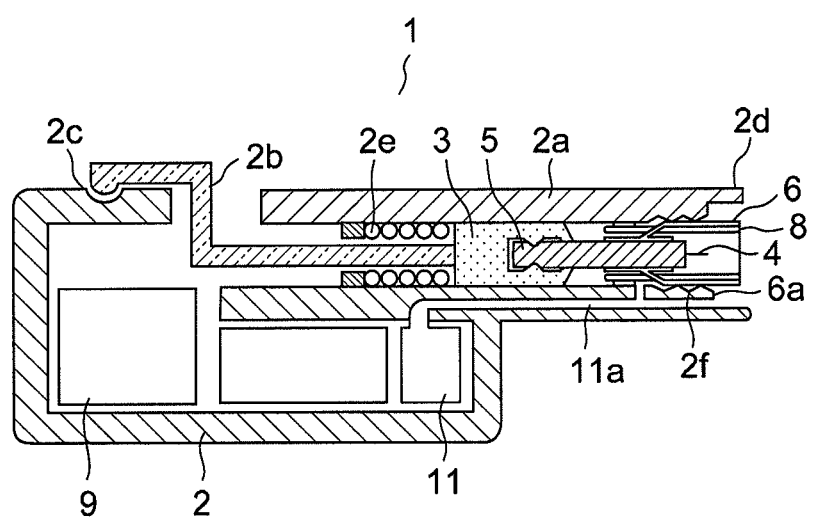
FIG. 26 is a cross-sectional view of the blood test apparatus with a negative pressure means.
Figure 27:
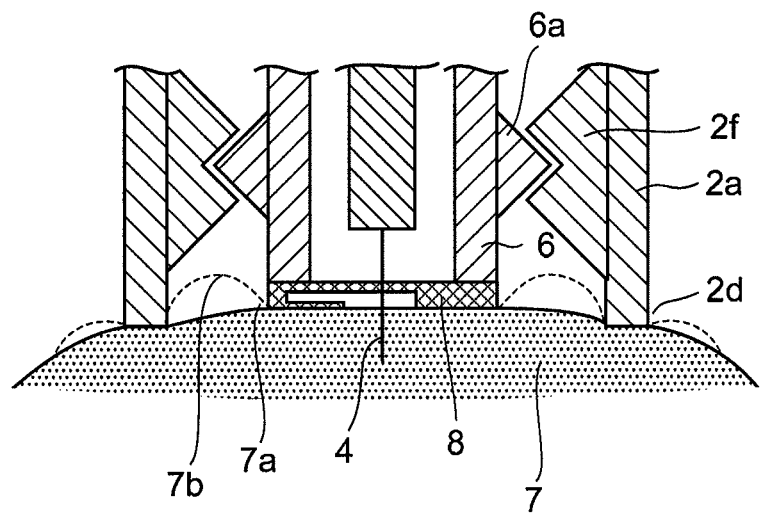
FIG. 27 is a cross-sectional view showing the vicinity of the punctured part in the blood test apparatus with a negative pressure means when the skin is punctured.
Figure 28:
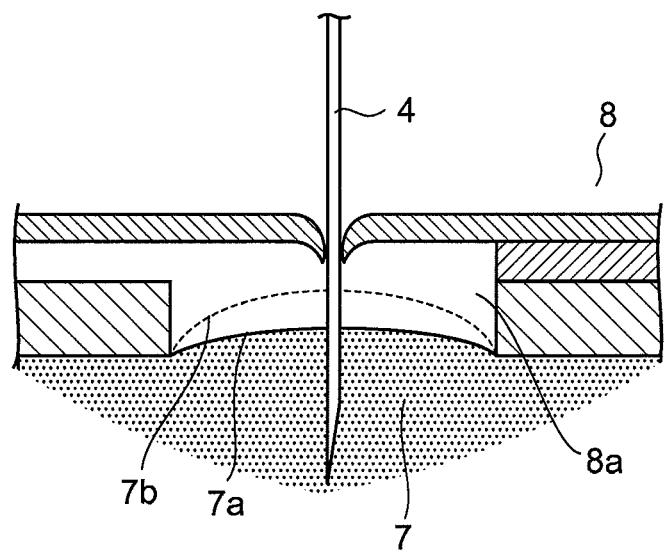
FIG. 28 is a cross-sectional view showing the vicinity of the storing part of the blood sensor in the blood test apparatus with a negative pressure means when the skin is punctured.

FIG. 24 is a block diagram showing measuring circuit 54 configuring blood test apparatus 50. Blood test apparatus 50 shown in FIG. 24 is attached with blood sensor 20-2.

In FIG. 24, terminals 103a to 103e are connected with connection electrodes 28a to 31a of blood sensor 20-2 and reference electrode 29h via connectors 47a to 47e, respectively. Terminals 103a to 103e are connected to switch circuit 121, and the output of switch circuit 121 is connected to the input of current/voltage converter 122. The output of current/voltage converter 72 is connected to the input of calculating section 124 via analogue/digital converter (hereinafter A/D converter) 123. The output of calculating section 124 is connected to display section 125 configured with liquid crystal or connected to the input of transmitting section 127. Further, reference voltage supply 128 is connected to switch circuit 121. Reference voltage supply 128 may be a ground potential.

The output of controlling section 126 of blood test apparatus 50 is connected to a controlling terminal of switch circuit 121, calculating section 124, transmitting section 127, timer 129 (see FIG. 24) and negative pressure means 55. The output of controlling section 126 may be connected to a warning means, puncturing button 57, fixing means 59 and 90, coil 81b and pulse motor 93a(not shown).

Further, the output of move detecting sensor 60 (see FIG. 1) is connected to the input of controlling section 126. It is also possible to use skin contact detecting sensors 60c and 60d (see FIG. 3) instead of move detecting sensor 60. The negative pressure means 55 supplies negative pressure to the negative pressure chamber 58 inside external cylinder body 51, and inside cartridge 42 via negative pressure path 58a.

In the case of using blood sensor 20-2 which has a reference electrode, before blood component is measured, it is specified to which of terminals 103a to 103e connection electrodes 28a to 31a are connected respectively. By a command from controlling section 126, terminal 103 having the electrical resistance between the neighboring terminal is a predetermined value (the electrical resistance is infinite in the case of blood sensor 20-1, the electrical resistance is zero in the case of blood sensor 20-2, and the electrical resistance is a set value in the case of blood sensor 20-3) is detected. The connection electrode connected to detected terminal 103 is specified as connection electrode 29a. Using terminal 103 connected to connection electrode 29a as a reference, each of terminals 103 connected to connection electrodes 30a, 31a and 28a, is specified in order. In this way, after terminals 103 connected to connection electrodes 28a to 31a are determined, the blood components are measured.

Switch circuit 121 is switched, and detection electrode 28 which serves as an active electrode for measuring the amount of blood components, is connected to current/voltage converter 122 via terminal 103b specified as described above. Further, detection electrode 29 which serves as a sensing electrode for detecting the inflow of blood 13, is connected to reference voltage supply 128 via terminal 103d specified as described above. A certain voltage is applied between detection electrode 28 and detection electrode 29. When blood 13 flows into the detecting section in this state, a current flows between detection electrode 28 and detection electrode 29. This current is converted to a voltage by current/voltage converter 122, and the voltage value is converted to a digital value by A/D converter 123. The converted digital value is outputted to calculating section 124. Calculating section 124 detects a sufficient inflow of blood 13 based on the digital value. When blood 13 is not detected at detecting section 27 after a predetermined time has passed or when the amount of blood 13 is not adequate, a warning means may be activated for warning the patient, or the measure may be displayed on display section 125.

Next, the amount of the glucose content, which is a blood component, is measured. First, by a command from controlling section 126, switch circuit 121 is switched, and detection electrode 28 as an active electrode for measuring the glucose content is connected to current/voltage converter 122 via terminal 103b specified as described above. Further, detection electrode 30, which serves as a counter electrode for measuring the glucose content, is connected to reference voltage supply 128 via terminal 103e specified as described above.

While the glucose in blood and the oxidation-reduction enzyme are reacted for a certain period, current/voltage converter 122 and reference voltage supply 128 are turned off. After a certain period (approximately 1 to 10 seconds) has passed, by a command from controlling section 126, a certain voltage (0.2 V to 0.5 V) is applied between detection electrode 28 and detection electrode 30. The current flowing between detection electrode 28 and detection electrode 30 is converted to a voltage by current/voltage converter 122. The voltage value is converted to a digital value by A/D converter 123 and outputted to calculating section 124. Calculating section 124 calculates the glucose content based on the digital value.

Next, the Hct level is measured. By a command from controlling section 126, switch circuit 121 is switched. Detection electrode 31, which serves as an active electrode for measuring the Hct level, is connected to current/voltage converter 122 via terminal 103a specified as described above, and detection electrode 28, which serves as a counter electrode for measuring the Hct level, is connected to reference voltage supply 128.

By a command from controlling section 126, a certain voltage (2 to 3 V) is applied between detection electrode 31 and detection electrode 28 from current/voltage converter 122 and reference voltage supply 128. A current flowing between detection electrode 31 and detection electrode 28 is converted to a voltage by current/voltage converter 122. The voltage value is converted to a digital value by A/D converter 123 and outputted to calculating section 124. Calculating section 124 calculates the Hct level based on this digital value.

Using the measured Hct level and the glucose content, and, with reference to the calibration curve or the calibration table, the glucose content is corrected based on the Hct level. The corrected result is displayed on display section 125.

Further, the corrected result may be transmitted from transmitting section 127 to an injection apparatus that injects insulin (used as an example of an antidote). The result may be transmitted by radio, but is preferably transmitted using optical communication which does not interfere with medical equipment. If the dose of insulin can be set to an injection apparatus automatically by transmitting the corrected measured data from transmitting section 127, the patient does not need to set the dose of insulin to the injection apparatus. Further, since the dose of insulin can be set to the injection apparatus without involving an artificial means, it is possible to prevent setting errors.

Although the blood test apparatus of the present invention has been described using an example of measuring glucose content, the blood test apparatus of the present invention is also applicable to measurement of the amount of blood components other than glucose (such as lactic acid and cholesterol).

INDUSTRIAL APPLICABILITY

According to the blood test apparatus of the present invention, by eliminating the difference in the amount of a plump of the skin, which is caused by hardness of the skin of the part to be punctured, test condition in a blood test can be fixed. Therefore, the present invention is applicable to medical equipment such as a blood test apparatus.

The disclosures of Japanese Patent Application No. 2006-032245 and Japanese Patent Application No. 2006-032246, filed on Feb. 9, 2006, including the specifications, drawings and abstracts are incorporated herein by reference in their entirety.

The invention claimed is:

1. A blood test apparatus comprising:
a housing which comprises a chassis;
an internal cylinder body which is provided at one side of the housing;
a reciprocator that moves back and forth inside the internal cylinder body;
a blood collection needle which is connected to the reciprocator;
a blood sensor to which the blood collection needle is directed and provided at a tip part of the internal cylinder body, the blood sensor having
a base plate;
a storage which is provided in the base plate and which collects blood from skin punctured with the blood collection needle;
a supply channel, one end of which is connected to the storage, and into which the blood in the storage flows by capillary action;
an air hole provided at an other end of the supply channel;
a detector provided inside the supply channel;
a plurality of detection electrodes which configure the detector; and
a plurality of connection electrodes provided on an outer periphery of the base plate being derived from each of the plurality of detection electrodes;
a measuring circuit to which a signal of the blood sensor is supplied;
a negative pressure provider which is drivable in dependence on the measuring circuit; and
an external cylinder body which covers the internal cylinder body and comprises an opening part at a tip side of the internal cylinder body, and is provided so as to be movable relative to the internal cylinder body and to return to a predetermined relative position,
wherein the negative pressure provider is configured to create a negative pressure inside the external cylinder body.

2. The blood test apparatus according to claim 1, wherein the external cylinder body covers the whole of the housing.

3. The blood test apparatus according to claim 1, further comprising a first fixer that fixes a position of the external cylinder body relative to the internal cylinder body.

4. The blood test apparatus according to claim 1, wherein the tip part of the internal cylinder body is in front of the opening part of the external cylinder body in the predetermined relative position.

5. The blood test apparatus according to claim 1, wherein the tip part of the internal cylinder body is behind the opening part of the external cylinder body in the predetermined relative position.

6. The blood test apparatus according to claim 1, wherein the reciprocator is driven by an elastic force of an elastic body.

7. The blood test apparatus according to claim 1, wherein the reciprocator is driven by an electromagnetic force.

8. The blood test apparatus according to claim 1, further comprising a second fixer that fixes the reciprocator to the external cylinder body or to the housing.

9. A method for examining blood using the blood test apparatus according to claim 8, comprising:
attaching the blood collection needle to the reciprocator to fix the reciprocator to the external cylinder body or to the housing by the the second fixer; and
puncturing the skin with the blood collection needle.

10. The blood test apparatus according to claim 1, further comprising a move detecting sensor that detects relative movement of the external cylinder body, or a skin contact detecting sensor that detects contact between a tip part of the external cylinder body and skin.

11. The blood test apparatus according to claim 10, wherein the move detecting sensor is a micro switch.

12. The blood test apparatus according to claim 10, wherein the move detecting sensor is an optical sensor.

13. The blood test apparatus according to claim 10, wherein the skin contact detecting sensor comprises two or more electrical conductors provided on the opening part of the external cylinder body.

14. The blood test apparatus according to claim 10, wherein the negative pressure section stops when the move detecting sensor detects a return of the external cylinder body to the predetermined relative position with respect to the internal cylinder, or when the skin contact detecting sensor detects a non-contact state of the skin.

15. The blood test apparatus according to claim 10, wherein the measuring circuit controls the negative pressure provider based on an output of the move detecting sensor or the skin contact detecting sensor.

16. A method for examining blood using the blood test apparatus according to claim 10, comprising
starting driving the negative pressure provider based on a signal from the move detecting sensor or the skin contact detecting sensor depending on the measuring circuit.

17. A method for examining blood using the blood test apparatus according to claim 10, comprising:
of starting driving the negative pressure provider based on a signal from the move detecting sensor or the skin contact detecting sensor depending on the measuring circuit;
fixing the position of the external cylinder body relative to the internal cylinder body by a first fixer; and
puncturing the skin with the blood collection needle.

18. A method for examining blood using the blood test apparatus according to claim 10, comprising stopping the negative pressure provider based on a signal from the move detecting sensor or the skin contact detecting sensor.

19. The blood test apparatus according to claim 1, wherein a material of part or whole of the opening part of the external cylinder body is an elastic body.

20. The blood test apparatus according to claim 1, wherein a material of a part or a whole of the opening part of the external cylinder body has low thermal conductivity.

21. The blood test apparatus according to claim 1, further comprising a timer and a display that are connected to the measuring circuit.

22. The blood test apparatus according to claim 21, wherein:
the timer measures a predetermined driving time of the negative pressure provider; and
the display displays that puncturing is allowed, after the predetermined driving time has passed.

23. The blood test apparatus according to claim 1, wherein:
the blood collection needle and the blood sensor are integrated in a holder and comprise a blood sampling cartridge; and
the blood sampling cartridge is removably attached to the internal cylinder body.

24. The blood test apparatus according to claim 1, wherein the storage of the blood sensor communicates with a negative pressure chamber provided inside the external cylinder body.

25. A method for examining blood using the blood test apparatus according to claim 1, comprising stopping the negative pressure provider based on signals from the detection electrodes.

26. A blood test apparatus comprising:
a housing which comprises a chassis;
an internal cylinder body which is provided at one side of the housing;
a reciprocator that moves back and forth inside the internal cylinder body;
a blood collection needle which is connected to the reciprocator;
a blood sensor to which the blood collection needle is directed and provided at a tip part of the internal cylinder body;
a measuring circuit to which a signal of the blood sensor is supplied;
a negative pressure provider which is drivable in dependence on the measuring circuit; and
an external cylinder body which covers the internal cylinder body and comprises an opening part at a tip side of the internal cylinder body, and is provided so as to be able to move relative to the internal cylinder body and to return to a predetermined relative position,
wherein the negative pressure provider is configured to create a negative pressure inside the external cylinder body, and
wherein the tip part of the internal cylinder body is behind the opening part of the external cylinder body in the predetermined relative position.

27. A blood test apparatus comprising:
a housing which comprises a chassis;
an internal cylinder body which is provided at one side of the housing;
a reciprocator that moves back and forth inside the internal cylinder body;
a blood collection needle which is connected to the reciprocator;
a blood sensor to which the blood collection needle is directed and provided at a tip part of the internal cylinder body;
a measuring circuit to which a signal of the blood sensor is supplied;
a negative pressure provider which is drivable in dependence on the measuring circuit;
an external cylinder body which covers the internal cylinder body and comprises an opening part at a tip side of the internal cylinder body, and is provided so as to be movable relative to the internal cylinder body and to return to a predetermined relative position; and
a move detecting sensor that detects the relative movement of the external cylinder body, or a skin contact detecting sensor that detects contact between a tip part of the external cylinder body and skin,
wherein the negative pressure provider is configured to create a negative pressure inside the external cylinder body, and
wherein the skin contact detecting sensor comprises two or more electrical conductors provided on the opening part of the external cylinder body.

28. A blood test apparatus comprising:
a housing which comprises a chassis;
an internal cylinder body which is provided at one side of the housing;
a reciprocator that moves back and forth inside the internal cylinder body;
a blood collection needle which is connected to the reciprocator;
a blood sensor to which the blood collection needle is directed and provided at a tip part of the internal cylinder body;
a measuring circuit to which a signal of the blood sensor is supplied;
a negative pressure provider which is drivable in dependence on the measuring circuit;
an external cylinder body which covers the internal cylinder body and comprises an opening part at a tip side of the internal cylinder body, and is provided so as to be movable relative to the internal cylinder body and to return to a predetermined relative position; and
a move detecting sensor that detects the relative movement of the external cylinder body, or a skin contact detecting sensor that detects contact between a tip part of the external cylinder body and skin,
wherein the negative pressure provider is configured to create a negative pressure inside the external cylinder body, and
wherein the negative pressure provider stops when the move detecting sensor detects a return of the external cylinder body to the predetermined relative position with respect to the internal cylinder, or when the skin contact detecting sensor detects a non-contact state of the skin.

29. A blood test apparatus comprising:
a housing which comprises a chassis;
an internal cylinder body which is provided at one side of the housing;
a reciprocator that moves back and forth inside the internal cylinder body;
a blood collection needle which is connected to the reciprocator;
a blood sensor to which the blood collection needle is directed and provided at a tip part of the internal cylinder body;
a measuring circuit to which a signal of the blood sensor is supplied;
a negative pressure provider which is movable in dependence on the measuring circuit;
an external cylinder body which covers the internal cylinder body and comprises an opening part at a tip side of the internal cylinder body, and is provided so as to be able to be movable relative to the internal cylinder body and to return to a predetermined relative position; and
a timer and a display that are connected to the measuring circuit,
wherein the negative pressure provider is configured to create a negative pressure inside the external cylinder body, and wherein the timer measures a predetermined driving time of the negative pressure provider, and the display displays that puncturing is allowed, after the predetermined driving time has passed.

30. A method for examining blood using a blood test apparatus including:
- a housing which comprises a chassis;
- an internal cylinder body which is provided at one side of the housing;
- a reciprocator that moves back and forth inside the internal cylinder body;
- a blood collection needle which is connected to the reciprocator;
- a blood sensor to which the blood collection needle is directed and provided at a tip part of the internal cylinder body;
- a measuring circuit to which a signal of the blood sensor is supplied;
- a negative pressure provider which is drivable in dependence on the measuring circuit;
- an external cylinder body which covers the internal cylinder body and comprises an opening part at a tip side of the internal cylinder body, and is provided so as to be movable relative to the internal cylinder body and to return to a predetermined relative position; and
- a move detecting sensor that detects the relative movement of the external cylinder body, or a skin contact detecting sensor that detects contact between a tip part of the external cylinder body and skin, wherein the negative pressure provider is configured to create a negative pressure inside the external cylinder body, and wherein the method comprises:

stopping the negative pressure provider based on a signal from the move detecting sensor or the skin contact detecting sensor.

* * * * *